United States Patent
Schwede et al.

(10) Patent No.: US 9,085,603 B2
(45) Date of Patent: Jul. 21, 2015

(54) PROGESTERONE RECEPTOR ANTAGONISTS

(75) Inventors: Wolfgang Schwede, Glienicke (DE); Ulrich Klar, Berlin (DE); Carsten Möller, Berlin (DE); Andrea Rotgeri, Berlin (DE); Wilhelm Bone, Berlin (DE); Christoph Huwe, Berlin (DE)

(73) Assignee: Bayer Intellectual Property GmbH, Monheim (DE)

( * ) Notice: Subject to any disclaimer, the term of this patent is extended or adjusted under 35 U.S.C. 154(b) by 289 days.

(21) Appl. No.: 13/577,799

(22) PCT Filed: Feb. 8, 2011

(86) PCT No.: PCT/EP2011/051781
§ 371 (c)(1),
(2), (4) Date: Sep. 21, 2012

(87) PCT Pub. No.: WO2011/098437
PCT Pub. Date: Aug. 18, 2011

(65) Prior Publication Data
US 2013/0005697 A1  Jan. 3, 2013

(30) Foreign Application Priority Data
Feb. 10, 2010 (DE) .......... 10 2010 007 722

(51) Int. Cl.
| | |
|---|---|
| A61K 31/58 | (2006.01) |
| A61K 31/567 | (2006.01) |
| C07J 1/00 | (2006.01) |
| C07J 43/00 | (2006.01) |
| C07J 41/00 | (2006.01) |
| A61K 31/573 | (2006.01) |

(52) U.S. Cl.
CPC ............ *C07J 43/003* (2013.01); *C07J 41/0083* (2013.01); *A61K 31/573* (2013.01); *A61K 31/58* (2013.01)

(58) Field of Classification Search
CPC .. C07J 43/003; C07J 41/0083; A61K 31/573; A61K 31/58
USPC .................. 552/648; 514/176, 179
See application file for complete search history.

(56) References Cited

U.S. PATENT DOCUMENTS

| | | | |
|---|---|---|---|
| 4,386,085 A | 5/1983 | Teutsch et al. | |
| 4,609,651 A | 9/1986 | Rohde et al. | |
| 4,900,725 A | 2/1990 | Nioue et al. | |
| 4,921,846 A | 5/1990 | Nedelec et al. | |
| 4,954,490 A | 9/1990 | Cook et al. | |
| 5,073,548 A | 12/1991 | Cook et al. | |
| 5,108,996 A | 4/1992 | Claussner et al. | |
| 5,272,140 A | 12/1993 | Loozen | |
| 5,407,928 A | 4/1995 | Kasch et al. | |
| 5,576,310 A | 11/1996 | Schubert et al. | |
| 5,693,628 A | 12/1997 | Schubert et al. | |
| 5,712,264 A | 1/1998 | Hamersma et al. | |
| 5,739,125 A | 4/1998 | Kasch et al. | |
| 5,986,115 A | 11/1999 | Bohlmann et al. | |
| 6,020,328 A | 2/2000 | Cook et al. | |
| 6,043,234 A | 3/2000 | Stockemann et al. | |
| 6,225,298 B1 | 5/2001 | Spicer et al. | |
| 6,316,432 B1 | 11/2001 | Schwede et al. | |
| 6,476,079 B1 | 11/2002 | Jukarainen et al. | |
| 6,503,895 B2 | 1/2003 | Schwede et al. | |
| 6,806,263 B2 | 10/2004 | Schwede et al. | |
| 6,825,182 B2 | 11/2004 | Ring et al. | |
| 6,861,415 B2 | 3/2005 | Kim et al. | |
| 7,087,591 B2 | 8/2006 | Kim et al. | |
| 7,148,213 B2 | 12/2006 | Schwede et al. | |
| 7,192,942 B2 | 3/2007 | Grawe et al. | |
| 7,550,451 B2 | 6/2009 | Hillisch et al. | |
| 7,799,770 B2 | 9/2010 | Grawe et al. | |
| 7,910,573 B2 | 3/2011 | Beckmann et al. | |
| 8,053,426 B2 | 11/2011 | Fuhrmann et al. | |
| 2001/0016578 A1 | 8/2001 | Spicer et al. | |
| 2002/0045774 A1 | 4/2002 | Schwede et al. | |
| 2002/0143000 A1 | 10/2002 | Hegele-Hartung et al. | |
| 2003/0069434 A1 | 4/2003 | Bohlmann et al. | |
| 2003/0191099 A1 | 10/2003 | Bohlmann et al. | |

(Continued)

FOREIGN PATENT DOCUMENTS

| | | |
|---|---|---|
| CA | 2280041 C | 8/1998 |
| EP | 57115 A2 | 8/1982 |

(Continued)

OTHER PUBLICATIONS

U. Fuhrmann et al., "Synthesis and Biological Activity of a Novel, Highly Potent Progesterone Receptor Antagonist," 43 J. Med. Chem. 5010-5016 (2000).

Van Geerstein et al., "Structure of the n-Butyl Acetate Solvate of 11β-[4-(Dimethylamino)phenyl]-17β-hydroxy-17α-(1-propynyl)estra-4,9-dien-3-one," Acta Cryst., C42, pp. 1521-1523 (1986).

Steinauer et al., "Systematic review of mifepristone for the treatment of uterine leiomyomata," Obstet Gynecol, vol. 103, No. 6, pp. 1331-1336 (Jun. 2004).

Chwalisz et al., "A randomized, controlled trial of asoprisnil, a novel selective progesterone receptor modulator, in women with uterine leiomyomata," Fertil Steril, vol. 87, No. 6, pp. 1399-1412 (Jun. 2007).

(Continued)

*Primary Examiner* — Barbara P Badio
(74) *Attorney, Agent, or Firm* — Karen B. King

(57) ABSTRACT

The invention relates to 17-hydroxy-17-pentafluoroethyl-estra-4,9(10)-dien-11-aryl derivatives of the formula I with a progesterone antagonizing effect and processes for their preparation, their use for the treatment and/or prophylaxis of diseases, and also their use for producing medicaments for the treatment and/or prophylaxis of diseases, in particular of uterus fibroids (myomas, uterine leiomyomas), endometriosis, heavy menstrual bleeding, meningiomas, hormone-dependent breast cancers and troubles associated with the menopause or for monitoring fertility and emergency contraception.

15 Claims, No Drawings

(56) References Cited

U.S. PATENT DOCUMENTS

| | | | |
|---|---|---|---|
| 2004/0006241 | A1 | 1/2004 | Grawe et al. |
| 2004/0048841 | A1 | 3/2004 | Hoffmann et al. |
| 2004/0157811 | A1 | 8/2004 | Lichtner et al. |
| 2005/0080060 | A1 | 4/2005 | Schwede et al. |
| 2005/0277769 | A1 | 12/2005 | Burton et al. |
| 2007/0105828 | A1 | 5/2007 | Joshi et al. |
| 2009/0075989 | A1 | 3/2009 | Schwede et al. |
| 2011/0112057 | A1 | 5/2011 | Fuhrmann et al. |
| 2012/0149670 | A1 | 6/2012 | Schwede et al. |
| 2012/0184515 | A1 | 7/2012 | Klar et al. |
| 2012/0190660 | A1 | 7/2012 | Klar et al. |
| 2012/0232042 | A1 | 9/2012 | Klar et al. |
| 2012/0258941 | A1 | 10/2012 | Klar et al. |
| 2012/0316145 | A1 | 12/2012 | Klar et al. |
| 2013/0072464 | A1 | 3/2013 | Schwede et al. |

FOREIGN PATENT DOCUMENTS

| | | |
|---|---|---|
| EP | 0411733 B1 | 2/1991 |
| EP | 0676203 A1 | 10/1995 |
| EP | 909764 A1 | 4/1999 |
| EP | 0970103 | 4/2002 |
| EP | 1862468 A1 | 12/2007 |
| IN | 978/MUM/2005 | 8/2005 |
| JP | H11171774 A | 6/1999 |
| WO | WO-96/03130 A1 | 2/1996 |
| WO | WO-96/15794 A1 | 5/1996 |
| WO | 9623503 A1 | 8/1996 |
| WO | 98/05679 A2 | 2/1998 |
| WO | WO-98/007740 A1 | 2/1998 |
| WO | 98/26783 A1 | 6/1998 |
| WO | 98/34947 A1 | 8/1998 |
| WO | WO-98/34947 A1 | 8/1998 |
| WO | WO-99/33855 A1 | 7/1999 |
| WO | 99/53924 A1 | 10/1999 |
| WO | 01/47490 A1 | 7/2001 |
| WO | WO-01/47490 A1 | 7/2001 |
| WO | 02/32429 A2 | 4/2002 |
| WO | WO-03/045972 A1 | 6/2003 |
| WO | 03/093292 A1 | 11/2003 |
| WO | 2006/010097 A2 | 1/2006 |
| WO | WO-2006/010097 A2 | 1/2006 |
| WO | 2008/058767 A1 | 5/2008 |
| WO | WO-2008058767 A1 | 5/2008 |
| WO | WO-2009138186 A2 | 11/2009 |
| ZA | 97/7482 | 2/1998 |

OTHER PUBLICATIONS

Kettel et al., "Endocrine responses to long-term administration of the antiprogesterone RU486 in patients with pelvic endometriosis," Fertil Steril, vol. 56, No. 3, pp. 402-407 (Sep. 1991).

Kettel et al., "Treatment of endometriosis with the antiprogesterone mifepristone (RU486)," Fertil Steril, vol. 65, No. 1, pp. 23-28 (Jan. 1996).

Kettel et al., "Preliminary report on the treatment of endometriosis with low-dose mifepristone (RU 486),". Am J Obstet Gynecol, vol. 178, No. 6, pp. 1151-1156 (Jun. 1998).

Möller et al., "Investigational developments for the treatment of progesterone-dependent diseases," Expert Opin. Investig. Drugs., vol. 17, No. 4, pp. 469-479 (2008).

Bagaria et al., Low-dose mifepristone in treatment of uterine leiomyoma: A randomised double-blind placebo-controlled clinical trial, The Royal Australian and New Zealand College of Obstetricians and Gynaecologists, vol. 49, pp. 77-83 (2009).

Murphy et al., "Regression of Uterine Leiomyomata in Response to the Antiprogesterone RU 486," J. Clin. Endocrinol. Metab., vol. 76, No. 2, pp. 513-517 (1993).

Bohl et al., "Molecular mechanics and X-ray crystal structure investigations on conformations of $11\beta$ substituted 4,9-dien-3-one steroids," J. Mol. Graphics, vol. 7, pp. 122-153 (Sep. 1989).

Braga et al., "3.3 Crystal Polymorphism: Challenges at the Crossroads of Science and Technology," Making Crystals By Design (Dario Braga and Fabrizia Grepioni eds., Wiley-VCH Verlag GmbH & Co. KgaA, Weinheim, Germany), pp. 293-314 (2007).

Cabri et al., "Polymorphisms and Patent, Market, and Legal Battles: Cefdinir Case Study," Organic Process Research & Devel., vol. 11, No. 1, pp. 64-72 (2007).

Caira, "Crystalline Polymorphism of Organic Compounds," Topics in Current Chemistry, vol. 198, pp. 164-208. (1998).

Davey, "Solvent Effects in Crystallization Processes," Current Topics in Material Science, vol. 8, pp. 429-479. (1982).

Hazra et al., "Mifepristone (RU-486), the recently developed antiprogesterone drug and its analogues," J. Indian Inst. Sci., vol. 81, pp. 287-298 (May-Jun. 2001).

Vippagunta et al., "Crystalline Solids," Adv. Drug Delivery Reviews, vol. 48, pp. 3-26 (2001).

Maibauer et al., "First human data for ZK 230211 (ZK-PRA), a new progesterone receptor antagonist: a phase I clinical analysis of safety and pharmacokinetics in healthy postmenopausal women," Abstracts-Poster Session IV, 29th Annual San Antonio Breast Cancer Symposium, Dec. 14-17, 2006.

Tellekson et al., "Strategies for Attacking and Defending Pharmaceutical Patents: A Modern Take on 'The Art of War,'" Int. Property & Techn. Law Journal, vol. 17, No. 12, pp. 5-14 (Dec. 2005).

Patani et al., "Bioisosterism: A Rational Approach in Drug Design," Chem. Rev., vol. 96, pp. 3147-3176 (1996).

English Language Translation of EP0411733, 1991.
English Language Translation of EP0676203, 1995.
English Language Translation of WO1998/026783, 1998.
English Language Translation of WO1999/053924, 1998.
English Language Abstract of JP H11171774, 1999.
English Transl. of Office Action for European Appl. No. 06 090 095 dated Jan. 16, 2007 (7,910,573 B2).

PROGESTERONE RECEPTOR ANTAGONISTS

RELATED APPLICATIONS

This application is a national stage application (under 35 U.S.C. §371) of PCT/EP2011/051781, filed Feb. 8, 2011, which claims benefit of German Application No. 10 2010 007 722.4, filed Feb. 10, 2010.

The invention relates to 17-hydroxy-17-pentafluoroethyl-estra-4,9(10)-dien-11-aryl derivatives of the formula I with a progesterone antagonising effect and processes for their preparation, their use for the treatment and/or prophylaxis of diseases, and also their use for producing medicaments for the treatment and/or prophylaxis of diseases, in particular of uterus fibroids (myomas, uterine leiomyomas), endometriosis, heavy menstrual bleeding, meningiomas, hormone-dependent breast cancers and troubles associated with the menopause or for monitoring fertility and emergency contraception.

These compounds are valuable pharmaceutical active ingredients. They can be used inter alia for producing pharmaceutical preparations for the treatment of uterus fibroids or endometriosis, heavy menstrual bleeding, meningiomas, hormone-dependent breast cancers and troubles associated with the menopause or for monitoring fertility and emergency contraception. For the treatment of uterus fibroids and endometriosis, the compounds according to the invention can also be administered sequentially in combination with gestagens. In such a treatment regime, the compounds according to the invention could be given over a period of 1-6 months, followed by a treatment break or a sequential treatment with a gestagen over a period of 2-6 weeks or followed by the treatment with an oral contraceptive (OC combinations) over the same period.

The effectiveness of the compounds according to the invention as progesterone receptor antagonist has been shown in vitro in transactivation tests and in vivo on rats (termination of early pregnancy).

Compounds with an antagonistic effect on the progesterone receptor (competitive progesterone receptor antagonists) have been known since 1982 (RU 486; EP57115) and have since been described widely. Progesterone receptor antagonists with a fluorinated 17α side chain were published in WO 98/34947 and Fuhrmann et al., J. Med. Chem. 43, 5010-5016 (2000).

The 4-substituent on the 11β-phenyl ring chosen in various clinical and preclinical progesterone receptor antagonists has been the dimethylamino functionality (e.g. mifepristone, onapristone, ulipristal, proellex). Advantages of the basic nitrogen atom are an increased solubility, particularly in the acidic aqueous medium, for example. As has been described several times, metabolic degradation of one or both methyl groups on the nitrogen atom releases compounds with an aromatic $NH_2$ group. These aniline metabolites can have potential side effects. Onapristone is a progesterone receptor antagonist with a dimethylamino functionality which is found in clinical studies. In some patients, abnormalities in liver function tests were observed which have ultimately led to the discontinuation of the clinical studies. Increased transaminase activities have also been described for mifepristone, the only progesterone receptor antagonist on the market which likewise carries a dimethylamino group in the 4-position of the 11β-phenyl radical. For both compounds, onapristone and mifepristone, compounds with partial or complete demethylation have been found as main metabolites. It was recently published that treatment with proellex in relatively high dosages likewise leads to an induction of liver enzymes.

It is an object of the present invention to provide highly potent competitive progesterone receptor antagonists which have the advantages of a basic nitrogen atom in the 4-position of the 11β-phenyl radical, but are unable to form free anilines as metabolites and thereby create alternative treatment options for gynaecological disorders.

This object was achieved by inserting a methylene group between the amino group and the 11β-phenyl radical. The compounds of general claim 1 are therefore particularly suitable for achieving this object. Whereas some of the compounds specified under claim 1 exhibit a slightly reduced antagonistic potency on the progesterone receptor compared to the analogous anilines, it has surprisingly been found that the incorporation of carbonyl functions or sulphonyl functions at a certain distance relative to the 11β-position of the steroid backbone leads to a considerable increase in the antagonistic potency. Some of these compounds also exhibit a very strong progesterone receptor antagonistic activity in preclinical in vivo experiments and an excellent selectivity in particular towards the glucocorticoid receptor. These compounds are therefore preferred. Mention is to be made particularly of the compounds described under the experimental examples 3, 11, 12, 13, 14 and 17, with exceptional in vivo properties in preclinical tests having been found particularly for the compounds described under examples 11 and 12.

The present invention relates to 17-hydroxy-17-pentafluoroethyl-estra-4,9(10)-dien-11-aryl derivatives with the general chemical formula I:

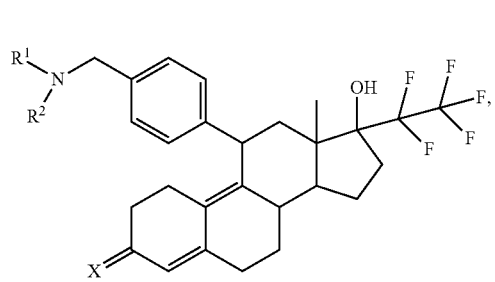

in which
$R^1$ and $R^2$
  are identical or different and are
  hydrogen,
  an optionally dimethylamine-substituted $C_1$-$C_{10}$-alkyl radical,
  a 6-10-membered aryl radical optionally mono-, di- or polysubstituted with halogen (—F, —Cl, —Br, —I), —OH, —O-alkyl, —C(O)OH, —C(O)Oalkyl, —C(O)$NH_2$, —C(O)NHalkyl, —C(O)Ndialkyl, —C(O)NHaryl, —C(O)NHheteroaryl, —$NH_2$, —NH($C_1$-$C_{10}$-alkyl), —N($C_1$-$C_{10}$-alkyl)$_2$, in particular —N($CH_3$)$_2$, —NHC(O)alkyl, —$NO_2$, —$N_3$, —CN, —$C_1$-$C_{10}$-alkyl, —$C_1$-$C_{10}$-perfluoroalkyl, —$C_1$-$C_{10}$-acyl, —$C_1$-$C_{10}$-acyloxy, —$SO_2NH_2$, —$SO_2$NHalkyl or —$SO_2$Ndialkyl,
  a 5-10-membered heteroaryl radical optionally mono-, di- or polysubstituted with the aforementioned substituents of the 6-10-membered aryl radical,
  a $C_1$-$C_6$-arylalkyl radical optionally mono-, di- or polysubstituted on the aryl ring with the aforementioned substituents of the 6-10-membered aryl radical or a $C_1$-$C_6$-heteroarylalkyl radical optionally mono-, di- or polysubstituted on the heteroaryl ring with the aforementioned substituents of the 6-10-membered aryl radical, or else $R^1$ and $R^2$ are together a constituent of a 3-10-membered ring which is optionally substituted on the carbon by alkyl, carboxyl, alkoxycarbonyl, alkylcarbonyl, aminocarbonyl, arylalkyl, heteroarylalkyl, aminoalkyl and/or on the nitrogen by alkyl, alkanoyl, carboxyl, alkoxycarbonyl, phenyl, phenylalkyl, pyridinyl, pyrimidinyl, pyrazinyl, sulphonyl, benzoyl, alkylsulphonyl, arylsulphonyl, aminocarbonyl, aminocarbonylalkyl, arylalkyl, heteroarylalkyl, heterocyclylalkyl and aminoalkyl, and which optionally contains nitrogen, oxygen or sulphur atoms which can optionally be oxidized with the sulphoxide or sulphone, where an aromatic can optionally be fused onto the 3-10-membered ring, X is an oxygen atom or $NOR^3$ or $NNHSO_2R^3$, $R^3$ is selected from the group comprising hydrogen, $C_1$-$C_{10}$-alkyl, aryl and their salts, solvates or solvates of the salts, including all crystal modifications.

The compounds of the general formula I according to the invention can exist in stereoisomeric forms (enantiomers, diastereomers) depending on their structure. The invention therefore encompasses the enantiomers or diastereomers and their respective mixtures including the racemates. The stereoisomerically uniform constituents can be isolated from such mixtures of enantiomers and/or diastereomers in a known manner.

Each of the specified substituents on the steroid basic backbone can be present either in an α position or in a β position.

If the compounds according to the invention are able to exist in tautomeric forms, the present invention includes all tautomeric forms.

Within the context of the present invention, preferred salts are physiologically acceptable salts of the compounds according to the invention. Also included, however, are salts which are themselves unsuitable for pharmaceutical applications but can be used, for example, for isolating or purifying the compounds according to the invention.

Physiologically acceptable salts of the compounds according to the invention include—if a basic function is present—salts with inorganic or organic acids, in particular of mineral acids, carboxylic acids and sulphonic acids, e.g. salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid. Physiologically acceptable salts of the compounds according to the invention include—if an acidic function is present—alkali metal salts, alkaline earth metal salts or ammonium salts, as can be obtained by reaction with corresponding inorganic or organic bases. By way of example and preferably, mention may be made of alkali metal salts (e.g. sodium and potassium salts), alkaline earth metal salts (e.g. calcium salts and magnesium salts) and ammonium salts derived from ammonia or organic amines having 1 to 16 carbon atoms, such as for example and preferably ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine, N-methylpiperidine, N-methylglucamine, D-methylglucamine, ethylglucamine, 1,6-hexadiamine, glucosamine, N-methylglycine, 2-amino-1,3-propanediol, tris-hydroxymethylaminomethane and 1-amino-2,3,4-butanetriol.

Within the context of the invention, solvates is the term used to refer to those forms of the compounds according to the invention which, in the solid or liquid state, exhibit an adduct formation with solvent molecules. The solvent here can be present in a stoichiometric ratio or in a nonstoichiometric ratio. In the case of stoichiometric solvates, the terms hemi-, (semi-), mono-, sesqui-, di-, tri-, tetra-, penta-, etc. solvates are also used. Hydrates are a specific form of the solvates in which the coordination takes place with water.

Moreover, the present invention also includes prodrugs of the compounds according to the invention. The term "prodrugs" includes compounds which are converted during their residence time in the body to compounds according to the invention, for example by enzymatic or hydrolytic processes.

Within the context of the present invention, unless specified otherwise, the substituents have the following meaning:

Alkyl is a straight-chain or branched-chain alkyl group having 1-6 carbon atoms, such as, for example, methyl, ethyl, propyl, isopropyl, n-butyl, sec-butyl, isobutyl, tert-butyl, n-pentyl, isopentyl, neopentyl, hexyl, heptyl, octyl, nonyl and decyl.

The alkyl radical can optionally be $C_1$-$C_4$-dialkylamine-substituted, in particular dimethylamine-substituted.

Aryl is a mono- to tricyclic aromatic, substituted or unsubstituted carbocyclic radical, such as, for example, phenyl or naphthyl.

The aryl radical can be mono-, di- or polysubstituted with halogen (—F, —Cl, —Br, —I), —OH, —O-alkyl, —$CO_2$H, —$CO_2$-alkyl, —C(O)$NH_2$, —C(O)NHalkyl, —C(O)Ndialkyl, —C(O)NHaryl, —C(O)NHheteroaryl, —$NH_2$, —NH($C_1$-$C_{10}$-alkyl), —N($C_1$-$C_{10}$-alkyl)$_2$, in particular —N($CH_3$)$_2$, —NHC(O)alkyl, —$NO_2$, —$N_3$, —CN, —$C_1$-$C_{10}$-perfluoroalkyl, —$C_1$-$C_{10}$-acyl, —$C_1$-$C_{10}$-acyloxy, —$SO_2NH_2$ or —$SO_2$NHalkyl, —$SO_2$Ndialkyl.

Heteroaryl is an aromatic, mono- or bicyclic radical having generally 5 to 10, preferably 5 to 6, ring atoms and up to 5, preferably up to 4, heteroatome from the series S, O and N, for example and preferably benzofuranyl, benzothiophenyl, quinolinyl, furyl, imidazolyl, indazolyl, indolyl, isoquinolinyl, oxazolyl, pyridazinyl, pyridyl, pyrimidyl, pyrrolyl, thiazolyl, thienyl, pyrazolyl, isoxazolyl, pyrazinyl, quinolyl or tetrazolyl.

The heteroaryl radical can be mono-, di- or polysubstituted with halogen (—F, —Cl, —Br, —I), —OH, —O-alkyl, —$CO_2$H, —$CO_2$-alkyl, —C(O)$NH_2$, —C(O)NHalkyl, —C(O)Ndialkyl, —C(O)NHaryl, —C(O)NHheteroaryl, —$NH_2$, —NH($C_1$-$C_{10}$-alkyl), —N($C_1$-$C_{10}$-alkyl)$_2$, in particular —N($CH_3$)$_2$, —NHC(O)alkyl, —$NO_2$, —$N_3$, —CN, —$C_1$-$C_{10}$-alkyl, —$C_1$-$C_{10}$-perfluoroalkyl, —$C_1$-$C_{10}$-acyl, —$C_1$-$C_{10}$-acyloxy, —$SO_2NH_2$ or —$SO_2$NHalkyl, —$SO_2$Ndialkyl.

Arylalkyl is arylalkyl groups which can contain in the ring up to 14 carbon atoms, preferably 6-10 carbon atoms, and in the alkyl chain 1-8, preferably 1-4, carbon atoms. Suitable arylalkyl radicals are, for example, benzyl, phenylethyl, naphthylmethyl or naphthylethyl.

The aryl moiety of the arylalkyl radical can be mono-, di- or polysubstituted halogen (—F, —Cl, —Br, —I), —OH, —O-alkyl, —$CO_2$H, —$CO_2$-alkyl, —C(O)$NH_2$, —C(O)NHalkyl, —C(O)Ndialkyl, —C(O)NHaryl, —C(O)NHheteroaryl, —$NH_2$, —NH($C_1$-$C_{10}$-alkyl), —N($C_1$-$C_{10}$-alkyl)$_2$, in particular —N($CH_3$)$_2$, —NHC(O)alkyl, —$NO_2$, —$N_3$, —CN, —C$_1$-C$_{10}$-alkyl, —C$_1$-C$_{10}$-perfluoroalkyl, —C$_1$-C$_{10}$-acyl, —C$_1$-C$_{10}$-acyloxy, —SO$_2$NH$_2$ or —SO$_2$NHalkyl, —SO$_2$Ndialkyl.

Heteroarylalkyl is heteroarylalkyl groups where heteroaryl has the meaning defined above and which can contain in the alkyl chain 1-8, preferably 1-4, carbon atoms. Suitable heteroarylalkyl radicals are, for example, furylmethyl, thienylethyl or pyridylpropyl.

The heteroaryl moiety of the heteroarylalkyl radical can be mono-, di- or polysubstituted with halogen (—F, —Cl, —Br, —I), —OH, —O-alkyl, —CO$_2$H, —CO$_2$-alkyl, —C(O)NH$_2$, —C(O)NHalkyl, —C(O)Ndialkyl, —C(O)NHaryl, —C(O)NHheteroaryl, —NH$_2$, —NH(C$_1$-C$_{10}$-alkyl), —N(C$_1$-C$_{10}$-alkyl)$_2$, in particular —N(CH$_3$)$_2$, —NHC(O)alkyl, —NO$_2$, —N$_3$, —CN, —C$_1$-C$_{10}$-alkyl, —C$_1$-C$_{10}$-perfluoroalkyl, C$_{1-10}$-acyl, —C$_1$-C$_{10}$-acyloxy, —SO$_2$NH$_2$ or —SO$_2$NHalkyl, —SO$_2$Ndialkyl.

If radicals are substituted in the compounds according to the invention, unless specified otherwise, the radicals may be mono- or polysubstituted. Within the context of the present invention, for all radicals which occur several times, their meaning is independent of one another. A substitution with one, two or three identical or different substituents is preferred. Very particular preference is given to substitution with one substituent.

For compounds in which R$^1$ and R$^2$ are together a constituent of an optionally substituted ring, this ring can be 3-10-membered and, as well as the nitrogen atom present, can carry only carbon atoms or else up to 2 further heteroatoms. Further heteroatoms to be mentioned are particularly optionally substituted nitrogen, oxygen, optionally oxidized sulphur. Suitable substituents on the carbon are alkyl groups, carboxyl groups, alkylcarboxyl groups, alkylcarbonyl groups, aminocarbonyl groups, arylalkyl groups, heteroarylalkyl groups, aminoalkyl groups. Suitable substituents on the nitrogen are particularly alkyl groups, alkanoyl groups, alkylcarboxyl groups, carboxyl groups, phenyl groups, phenylalkyl groups, pyridinyls, pyrimidinyls, pyrazinyls, sulphonyl groups, benzoyl groups, alkyl- or arylsulphonyl, aminocarbonyl, arylalkyl, heteroarylalkyl and aminoalkyl. Sulphur atoms in the ring can be oxidized to the sulphoxide or sulphone. An aromatic can optionally be fused onto the 3-10-membered ring.

Rings which are formed by R$^1$ and R$^2$ together are in particular piperidines, piperazines, morpholines, diazepanes, thiomorpholines, dioxidothiomorpholines, tetrahydropyrroles.

Within the context of the invention, heterocyclyl is a non-aromatic mono- or bicyclic ring system with at least one heteroatom or one hetero group. Nitrogen atoms, oxygen atoms and/or sulphur atoms can occur as heteroatoms. Hetero groups which may occur are —S(O)—, —S(O)$_2$—.

Heterocyclylalkyl is heterocyclylalkyl groups, where heterocyclyl has the meaning defined above and which can contain in the alkyl chain 1-6, preferably 1-4, carbon atoms. Suitable heterocyclylalkyl radicals are, for example, pyrrolidinoethyl.

A monocyclic heterocyclyl ring according to the present invention can have 3 to 8, preferably 5 to 8, particularly preferably 5 or 6, ring atoms. By way of example of monocyclic heterocyclyl radicals having 5 ring atoms, mention may be made of: pyrrolidinyl, imidazolidinyl, pyrazolidinyl, pyrrolinyl and tetrahydrofuranyl. By way of example of monocyclic heterocyclyl radicals having 6 ring atoms, mention may be made of: piperidinyl, piperazinyl, morpholinyl, tetrahydropyranyl and thiomorpholinyl.

A bicyclic heterocyclyl radical according to the present invention can have 5 to 12, preferably 8 to 10, ring atoms.

Preference is given to 5- to 8-membered, monocyclic saturated heterocyclyl radicals having up to two heteroatoms from the series O, N and S. Particular preference is given to morpholinyl, piperidinyl and pyrrolidinyl.

The radical definitions given specifically in the respective combinations and/or preferred combinations of radicals are, independently of the particular stated combinations of the radicals, replaced arbitrarily also by radical definitions of other combination.

Very particular preference is given to combinations of two or more of the aforementioned preferred ranges.

17-Hydroxy-17-pentafluoroethyl-estra-4,9(10)-dien-11-aryl derivatives with the general chemical formula II:

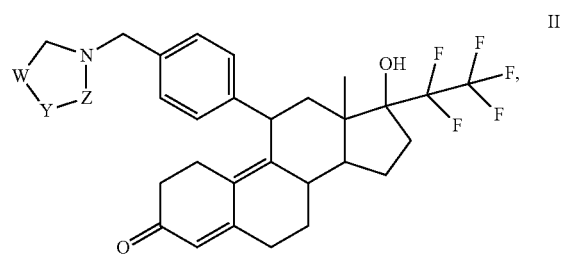

in which
Z is —CH$_2$—, —CH$_2$—CH$_2$— or —CH$_2$—CH$_2$—CH$_2$—,
W is —CH$_2$—,
Y is —CHR$^4$—, —NR$^5$—, —O— or —SO$_2$— or
W and Y
   together are a constituent of a fused aromatic ring,
R$^4$ and R$^6$
   are hydrogen, —C$_1$-C$_4$-alkyl, —(CH$_2$)$_m$-phenyl, —(CH$_2$)$_m$-pyridinyl, —(CH$_2$)$_m$-pyrazinyl, —(CH$_2$)$_m$—NR$^7$R$^8$, —(CH$_2$)$_m$—C(O)—R$^6$ where m=0, 1, 2 or 3 or —SO$_2$—C$_1$-C$_4$-alkyl,
R$^6$ is —OH, —C$_1$-C$_4$-alkyl, —O—C$_1$-C$_4$-alkyl, -phenyl or —NR$^7$R$^8$ and
R$^7$, R$^8$ independently of one another are hydrogen or —C$_1$-C$_4$-alkyl or together are a constituent of a 5- to 7-membered ring
and its salts, solvates or solvates of the salts, including all crystal modifications,
in particular the compounds:
(11β,17β)-17-hydroxy-11-{4-[(4-methylpiperazin-1-yl)methyl]phenyl}-17-(pentafluoroethyl)estra-4,9-dien-3-one (Example 2)
tert-butyl-4-{-44-[(11β,17β)-17-hydroxy-3-oxo-17-(pentafluoroethyl)estra-4,9-dien-11-yl]benzyl}piperazine-1-carboxylate (Example 3)
(11β,17β)-17-hydroxy-17-(pentafluoroethyl)-11-[4-(piperidin-1-ylmethyl)phenyl]estra-4,9-dien-3-one (Example 4)
methyl 1-{4-[(11β,17β)-17-hydroxy-3-oxo-17-(pentafluoroethyl)estra-4,9-dien-11-yl]benzyl}piperidine-4-carboxylate (Example 5)
tert-butyl 4-{4-[(11β,17β)-17-hydroxy-3-oxo-17-(pentafluoroethyl)estra-4,9-dien-11-yl]benzyl}-1,4-diazepane-1-carboxylate (Example 6)
(11β,17β)-17-hydroxy-11-[4-(morpholin-4-ylmethyl)phenyl]-17-(pentafluoroethyl)estra-4,9-dien-3-one (Example 7)
(11β,17β)-11-{4-[(1,1-dioxidothiomorpholin-4-yl)methyl]phenyl}-17-hydroxy-17-(pentafluoroethyl)estra-4,9-dien-3-one (Example 8)

(11β,17β)-17-hydroxy-17-(pentafluoroethyl)-11-[4-(piperazin-1-ylmethyl)phenyl]estra-4,9-dien-3-one (Example 10)

(11β,17β)-11-{4-[(4-acetylpiperazin-1-yl)methyl]phenyl}-17-hydroxy-17-(pentafluoroethyl)estra-4,9-dien-3-one (Example 11)

(11β,17β)-17-hydroxy-11-(4-{[4-(methylsulphonyl)piperazin-1-yl]methyl}phenyl)-17-(pentafluoroethyl)estra-4,9-dien-3-one (Example 12)

(11β,17β)-11-{4-[(4-benzoylpiperazin-1-yl)methyl]phenyl}-17-hydroxy-17-(pentafluoroethyl)estra-4,9-dien-3-one (Example 13)

(11β,17β)-11-(4-{[ 4-(2,2-dimethylpropanoyl)piperazin-1-yl]methyl}phenyl)-17-hydroxy-17-(pentafluoroethyl)estra-4,9-dien-3-one (Example 14)

1-{4-[(11β,17β)-17-hydroxy-3-oxo-17-(pentafluoroethyl)estra-4,9-dien-11-yl]benzyl}piperidine-4-carboxylic acid (Example 15)

(11β,17β)-11-[4-(1,4-diazepan-1-ylmethyl)phenyl]-17-hydroxy-17-(pentafluoroethyl)estra-4,9-dien-3-one (Example 16)

(11β,17β)-11-{4-[(4-acetyl-1,4-diazepan-1-yl)methyl]phenyl}-17-hydroxy-17-(pentafluoroethyl)estra-4,9-dien-3-one (Example 17)

(11β,17β)-17-hydroxy-17-(pentafluoroethyl)-11-{4-[(4-phenylpiperazin-1-yl)methyl]phenyl}estra-4,9-dien-3-one (Example 25)

(11β,17β)-11-[4-(3,4-dihydroisoquinolin-2(1H)-ylmethyl)phenyl]-17-hydroxy-17-(pentafluoroethyl)estra-4,9-dien-3-one (Example 30)

(11β,17β)-11-{4-[(4-benzylpiperazin-1-yl)methyl]phenyl}-17-hydroxy-17-(pentafluoroethyl)estra-4,9-dien-3-one (Example 31)

(11β,17β)-17-hydroxy-17-(pentafluoroethyl)-11-(4-{[4-(2-phenylethyl)piperazin-1-yl]methyl}phenyl)estra-4,9-dien-3-one (Example 34)

(11β,17β)-17-hydroxy-17-(pentafluoroethyl)-11-(4-{[4-(pyrazin-2-yl)piperazin-1-yl]methyl}phenyl)estra-4,9-dien-3-one (Example 35)

(11β,17β)-17-hydroxy-17-(pentafluoroethyl)-11-[4-({4-[2-(pyrrolidin-1-yl)ethyl]piperazin-1-yl}methyl)phenyl]estra-4,9-dien-3-one (Example 36)

(11β,17β)-17-hydroxy-17-(pentafluoroethyl)-11-(4-{[4-(pyridin-4-ylmethyl)piperazin-1-yl]methyl}phenyl)estra-4,9-dien-3-one (Example 37)

(11β,17β)-17-hydroxy-17-(pentafluoroethyl)-11-{4-[(4-phenylpiperidin-1-yl)methyl]phenyl}estra-4,9-dien-3-one (Example 41)

4-{4-[(11β,17β)-17-hydroxy-3-oxo-17-(pentafluoroethyl)estra-4,9-dien-11-yl]benzyl}-N,N-dimethylpiperazine-1-carboxamide (Example 42)

(11β,17β)-17-hydroxy-17-(pentafluoroethyl)-11-(4-{[4-(pyridin-2-ylmethyl)piperazin-1-yl]methyl}phenyl)estra-4,9-dien-3-one (Example 43)

(11β,17β)-17-hydroxy-17-(pentafluoroethyl)-11-(4-{[4-(pyridin-3-ylmethyl)piperazin-1-yl]methyl}phenyl)estra-4,9-dien-3-one (Example 44)

2-(4-{4-[(11β,17β)-17-hydroxy-3-oxo-17-(pentafluoroethyl)estra-4,9-dien-11-yl]benzyl}piperazin-1-yl)-N-methylacetamide (Example 45)

(11β,17β)-17-hydroxy-17-(pentafluoroethyl)-11-[4-(pyrrolidin-1-ylmethyl)phenyl]estra-4,9-dien-3-one (Example 46)

(11β,17β)-17-hydroxy-17-(pentafluoroethyl)-11-(4-{[4-(pyridin-4-yl)piperazin-1-yl]methyl}phenyl)estra-4,9-dien-3-one (Example 50) and (11β,17β)-11-[4-({4-[2-(dimethylamino)ethyl]piperazin-1-yl}methyl)phenyl]-17-hydroxy-17-(pentafluoroethyl)estra-4,9-dien-3-one (Example 51) are likewise preferred.

Particular preference is given to compounds of the formula II in which either —$C_1$-$C_4$-alkyl is methyl and/or in which Z: —$CH_2$—$CH_2$— and Y: —$NR^5$—, in particular those in which additionally $R^5$: —C(O)—$R^6$, and their salts, solvates or solvates of the salts, including all crystal modifications.

Preference is likewise given to the compounds of the general formula II in which Z is —$CH_2$—$CH_2$— or —$CH_2$—$CH_2$—$CH_2$—,
W is —$CH_2$—,
Y is —$CHR^4$—, —$NR^5$—,
$R^4$ and $R^5$
  are —C(O)—$R^6$ or —$SO_2$—$C_1$-$C_4$-alkyl and
$R^6$ is —OH, —$C_1$-$C_4$-alkyl,
and its salts, solvates or solvates of the salts, including all crystal modifications.

Preference is likewise given to 17-hydroxy-17-pentafluoroethyl-estra-4,9(10)-dien-11-aryl derivatives with the general chemical formula III:

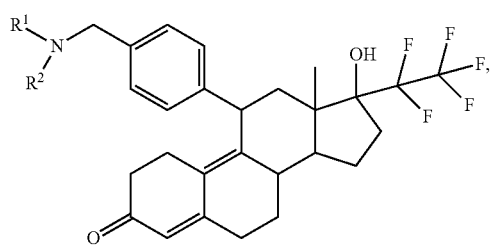

in which
$R^1$ and $R^2$
  are identical or different and, independently of one another, are hydrogen, $C_1$-$C_4$-alkyl radical, di—$C_1$-$C_4$-alkylamino—$C_1$-$C_4$-alkyl radical, an optionally halogen-, $C_1$-$C_4$-alkoxy-, —$SO_2NH_2$—, —C(O)$NH_2$—, —C(O)O—$C_1$-$C_4$-alkyl-, —NH—C(O)—$C_1$-$C_4$-alkyl- or —C(O)—NH-phenyl-substituted phenyl or $C_1$-$C_4$alkylphenyl radical or an optionally halogen-, $C_1$-$C_4$-alkoxy-, —$SO_2NH_2$—, —C(O)$NH_2$—, —C(O)O—$C_1$-$C_4$-alkyl-, —NH—C(O)—$C_1$-$C_4$-alkyl- or —C(O)—NH-phenyl-substituted pyridyl or $C_1$-$C_4$-alkylpyridyl radical, and its salts, solvates or solvates of the salts, including all crystal modifications.

Preference is moreover given to 17-hydroxy-17-pentafluoroethyl-estra-4,9(10)-dien-11-aryl derivatives with the general chemical formula III in which
$R^1$ is hydrogen or $C_1$-$C_4$-alkyl and
$R^2$ is hydrogen;
  dimethylamino—$C_1$-$C_4$-alkyl,
  an optionally halogen-, alkoxy-, —$SO_2NH_2$—, —C(O)$NH_2$—, —C(O)O—$C_1$-$C_4$-alkyl-, —NH—C(O)—$C_1$-$C_4$-alkyl- or —C(O)—NH-phenyl-substituted phenyl radical,
  —$C_1$-$C_4$-alkylphenyl,
  pyridyl or
  —$C_1$-$C_4$-alkylpyridyl
and its salts, solvates or solvates of the salts, including all crystal modifications.

Preference is moreover given to 17-hydroxy-17-pentafluoroethyl-estra-4,9(10)-dien-11-aryl derivatives with the general chemical formula III in which $R^1$ is hydrogen, methyl or ethyl, and their salts, solvates or solvates of the salts, including all crystal modifications.

Preference is moreover given to 17-hydroxy-17-pentafluoroethyl-estra-4,9(10)-dien-11-aryl derivatives with the general chemical formula III in which
$R^2$ is —$CH_3$, —$CH_2CH_3$, —$CH_2$—$CH_2$—$N(CH_3)_2$, a —$(CH_2)_n$-phenyl radical optionally substituted on the phenyl ring with Cl—, —$OCH_3$, —$SO_2NH_2$, —$C(O)NH_2$, —$C(O)OCH_3$, —NH—$C(O)CH_3$ or —$C(O)$—NH-phenyl, or a —$(CH_2)_n$-pyridyl where n=0, 1, 2,
and their salts, solvates or solvates of the salts, including all crystal modifications.

Preference is likewise given to 17-hydroxy-17-pentafluoroethyl-estra-4,9(10)-dien-11-aryl derivatives with the general chemical formula III in which
$R^1$ is hydrogen, methyl or ethyl and
$R^2$ is —$CH_3$, —$CH_2CH_3$, —$CH_2$—$CH_2$—$N(CH_3)_2$, a —$(CH_2)_n$-phenyl radical optionally substituted on the phenyl ring with Cl—, —$OCH_3$, —$SO_2NH_2$, —$C(O)NH_2$, —$CO_2CH_3$, —NH—$C(O)CH_3$ or —$C(O)$—NH-phenyl, or a —$(CH_2)_n$-pyridyl where n=0, 1, 2
and their salts, solvates or solvates of the salts, including all crystal modifications.

Preference is likewise given to 17-hydroxy-17-pentafluoroethyl-estra-4,9(10)-dien-11-aryl derivatives with the general chemical formula III, namely:

(11β,17β)-11-{4-[(dimethylamino)methyl]phenyl}-17-hydroxy-17-(pentafluoroethyl)estra-4,9-dien-3-one (Example 1)

(11β,17β)-17-hydroxy-17-(pentafluoroethyl)-11-(4-{[(2-phenylethyl)amino]methyl}phenyl)estra-4,9-dien-3-one (Example 9)

4-({4-[(11β,17β)-17-hydroxy-3-oxo-17-(pentafluoroethyl)estra-4,9-dien-11-yl]benzyl}amino)benzenesulphonamide (Example 18)

(11β,17β)-17-hydroxy-17-(pentafluoroethyl)-11-{4-[(pyridin-3-ylamino)methyl]phenyl}estra-4,9-dien-3-one (Example 19)

(11β,17β)-11-[4-(aminomethyl)phenyl]-17-hydroxy-17-(pentafluoroethyl)estra-4,9-dien-3-one (Example 20)

(11β,17β)-17-hydroxy-11-(4-{[(2-methoxyphenyl)amino]methyl}phenyl)-17-(pentafluoroethyl)estra-4,9-dien-3-one (Example 21)

(11β,17β)-17-hydroxy-11-(4-{[(3-methoxyphenyl)amino]methyl}phenyl)-17-(pentafluoroethyl)estra-4,9-dien-3-one (Example 22)

(11β,17β)-11-(4-{[(4-chlorophenyl)amino]methyl}phenyl)-17-hydroxy-17-(pentafluoroethyl)estra-4,9-dien-3-one (Example 23)

(11β,17β)-11-{4-[(diethylamino)methyl]phenyl}-17-hydroxy-17-(pentafluoroethyl)estra-4,9-dien-3-one (Example 24)

(11β,17β)-17-hydroxy-11-(4-{[methyl(pyridin-4-ylmethyl)amino]methyl}phenyl)-17-(pentafluoroethyl)estra-4,9-dien-3-one (Example 26)

(11β,17β)-11-[4-({[2-(dimethylamino)ethyl](methyl)amino}methyl)phenyl]-17-hydroxy-17-(pentafluoroethyl)estra-4,9-dien-3-one (Example 27)

methyl 2-({4-[(11β,17β)-17-hydroxy-3-oxo-17-(pentafluoroethyl)estra-4,9-dien-11-yl]benzyl}amino)benzoate (Example 28)

methyl 4-({4-[(11β,17β)-17-hydroxy-3-oxo-17-(pentafluoroethyl)estra-4,9-dien-11-yl]benzyl}amino)benzoate (Example 29)

4-({4-[(11β,17β)-17-hydroxy-3-oxo-17-(pentafluoroethyl)estra-4,9-dien-11-yl]benzyl}amino)benzamide (Example 32)

(11β,17β)-17-hydroxy-11-(4-{[methyl(2-phenylethyl)amino]methyl}phenyl)-17-(pentafluoroethyl)estra-4,9-dien-3-one (Example 33)

N-[4-({4-[(11β,17β)-17-hydroxy-3-oxo-17-(pentafluoroethyl)estra-4,9-dien-11-yl]benzyl}amino)phenyl]acetamide (Example 38)

methyl 3-({4-[(11β,17β)-17-hydroxy-3-oxo-17-(pentafluoroethyl)estra-4,9-dien-11-yl]benzyl}amino)benzoate (Example 39)

3-({-4-[(11β,17β)-17-hydroxy-3-oxo-17-(pentafluoroethyl)estra-4,9-dien-11-yl]benzyl}amino)benzenesulphonamide (Example 40)

(11β,17β)-17-hydroxy-17-(pentafluoroethyl)-11-(4-{[(pyridin-4-ylmethyl)amino]methyl}phenyl)estra-4,9-dien-3-one (Example 47)

(11β,17β)-17-hydroxy-11-(4-{[methyl(phenyl)amino]methyl}phenyl)-17-(pentafluoroethyl)estra-4,9-dien-3-one (Example 48)

2-({4-[(11β,17β)-17-hydroxy-3-oxo-17-(pentafluoroethyl)estra-4,9-dien-11-yl]benzyl}amino)benzamide (Example 49)

(11β,17β)-17-hydroxy-11-[4-({methyl[2-(pyridin-2-yl)ethyl]amino}methyl)phenyl]-17-(pentafluoroethyl)estra-4,9-dien-3-one (Example 52)

3-({4-[(11β,17β)-17-hydroxy-3-oxo-17-(pentafluoroethyl)estra-4,9-dien-11-yl]benzyl}amino)benzamide (Example 53)

4-({-4-[(11β,17β)-17-hydroxy-3-oxo-17-(pentafluoroethyl)estra-4,9-dien-11-yl]benzyl}amino)-N-phenylbenzamide (Example 54).

It has been found that the compounds and/or derivatives according to the invention have a good progesterone antagonising effect. In several clinical studies, it has been found that treatment with progesterone receptor antagonists (mifepristone, asoprisnil, proellex) can lead to a significant shrinkage of uterus fibroids and to a significant reduction in the symptoms associated with these uterus fibroids. Furthermore, in clinical studies, it has been shown that the symptoms caused by endometriosis (in particular pain) can also be significantly reduced as a result of treatment with the stated progesterone receptor antagonists.

The compounds of the general formula I and their physiologically compatible and pharmaceutically acceptable salts can be formulated by processes known to the person skilled in the art, with oral, once daily dosage forms being preferred.

Scheme 1

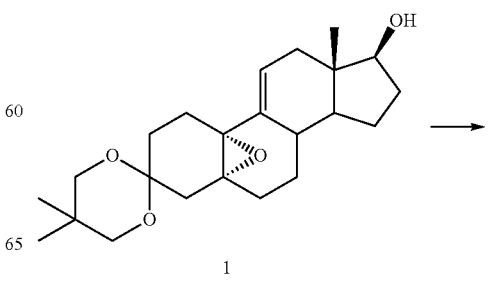

1

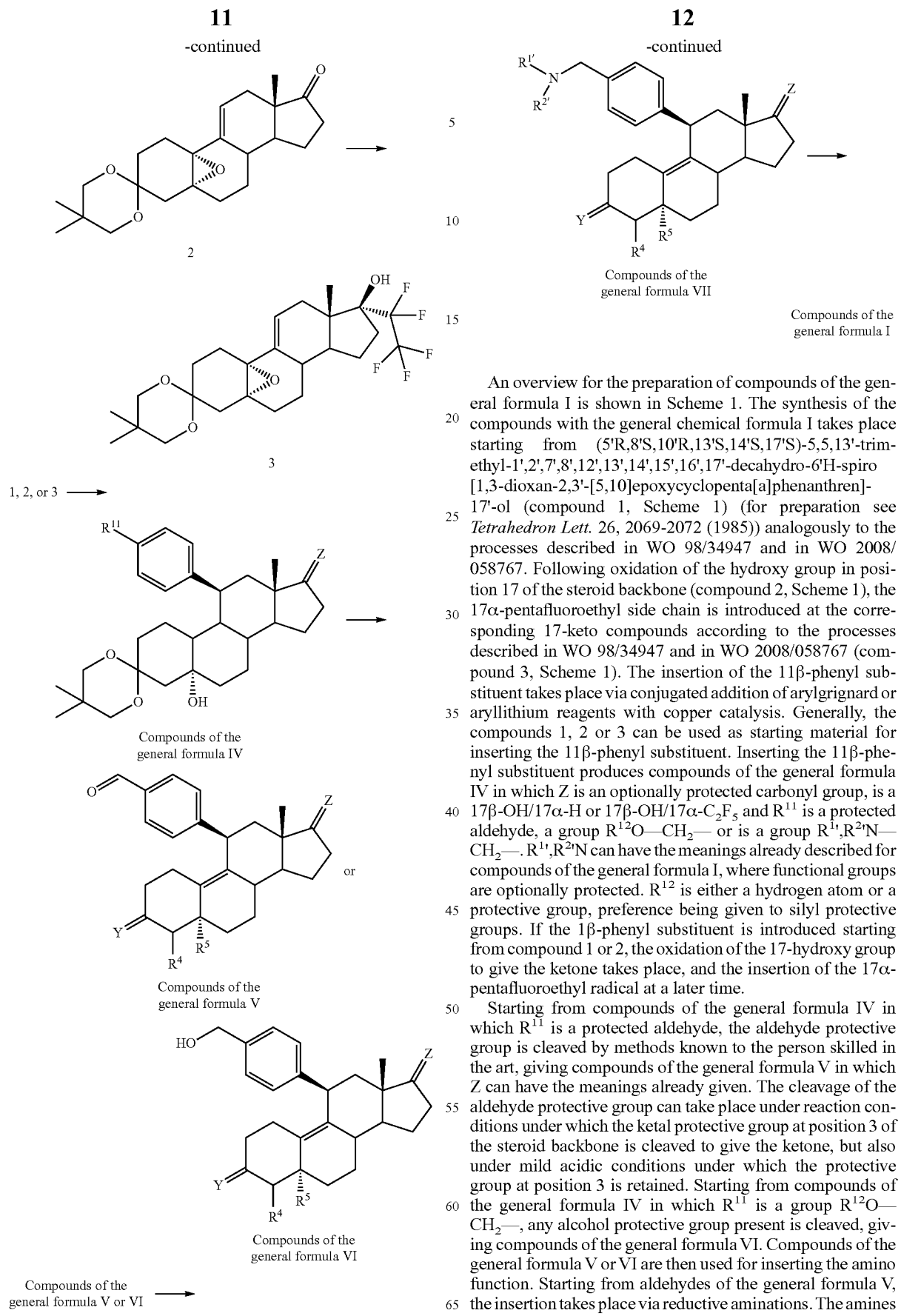

Compounds of the general formula VII

Compounds of the general formula I

An overview for the preparation of compounds of the general formula I is shown in Scheme 1. The synthesis of the compounds with the general chemical formula I takes place starting from (5'R,8'S,10'R,13'S,14'S,17'S)-5,5,13'-trimethyl-1',2',7',8',12',13',14',15',16',17'-decahydro-6'H-spiro[1,3-dioxan-2,3'-[5,10]epoxycyclopenta[a]phenanthren]-17'-ol (compound 1, Scheme 1) (for preparation see Tetrahedron Lett. 26, 2069-2072 (1985)) analogously to the processes described in WO 98/34947 and in WO 2008/058767. Following oxidation of the hydroxy group in position 17 of the steroid backbone (compound 2, Scheme 1), the 17α-pentafluoroethyl side chain is introduced at the corresponding 17-keto compounds according to the processes described in WO 98/34947 and in WO 2008/058767 (compound 3, Scheme 1). The insertion of the 11β-phenyl substituent takes place via conjugated addition of arylgrignard or aryllithium reagents with copper catalysis. Generally, the compounds 1, 2 or 3 can be used as starting material for inserting the 11β-phenyl substituent. Inserting the 11β-phenyl substituent produces compounds of the general formula IV in which Z is an optionally protected carbonyl group, is a 17β-OH/17α-H or 17β-OH/17α-C$_2$F$_5$ and R$^{11}$ is a protected aldehyde, a group R$^{12}$O—CH$_2$— or is a group R$^{1'}$,R$^{2'}$N—CH$_2$—. R$^{1'}$,R$^{2'}$N can have the meanings already described for compounds of the general formula I, where functional groups are optionally protected. R$^{12}$ is either a hydrogen atom or a protective group, preference being given to silyl protective groups. If the 1β-phenyl substituent is introduced starting from compound 1 or 2, the oxidation of the 17-hydroxy group to give the ketone takes place, and the insertion of the 17α-pentafluoroethyl radical at a later time.

Starting from compounds of the general formula IV in which R$^{11}$ is a protected aldehyde, the aldehyde protective group is cleaved by methods known to the person skilled in the art, giving compounds of the general formula V in which Z can have the meanings already given. The cleavage of the aldehyde protective group can take place under reaction conditions under which the ketal protective group at position 3 of the steroid backbone is cleaved to give the ketone, but also under mild acidic conditions under which the protective group at position 3 is retained. Starting from compounds of the general formula IV in which R$^{11}$ is a group R$^{12}$O—CH$_2$—, any alcohol protective group present is cleaved, giving compounds of the general formula VI. Compounds of the general formula V or VI are then used for inserting the amino function. Starting from aldehydes of the general formula V, the insertion takes place via reductive aminations. The amines used for this purpose may be primary or secondary and optionally carry protective groups. If the insertion of the amino group takes place starting from alcohols of the general formula IV, then the hydroxy group is firstly converted to a suitable escape group and this is then substituted by reaction with the corresponding amines. Suitable escape groups are, as well as chlorine, bromine or iodine, particularly tosylates or mesylates.

Compounds of the general formula I can then be prepared from the compounds of the general formula VII. For this purpose, any protective groups present are cleaved, and the radicals $R^{1\prime}$ and $R^{2\prime}$ are optionally further modified. Reactions of the radicals $R^{1\prime}$ and $R^{2\prime}$ to be mentioned are particularly oxidations or reductions, esterifications, saponifications, alkylation, acylations of free valences on the nitrogen, and also formations of sulphonamides.

Ketal protective or acetal protective groups to be mentioned are, for example, the ethylenedioxy group or the 2,2-dimethylpropylene-1,2-dioxy group. Hydroxy groups are protected for example in the form of methoxymethyl, methoxyethyl, tetrahydropyranyl, benzyl or silyl ethers.

During the cleavage of the 3-ketal to the 3-keto group of the steroid backbone, any 5α-hydroxy group still present is eliminated such that compounds of the general formula I are formed.

If the preparation of the starting compounds is not described here, these are known to the person skilled in the art or can be prepared analogously to known compounds or processes described here. The isomer mixtures can be separated into the individual compounds by customary methods, such as, for example, crystallization, chromatography or salt formation. The salts are prepared in the customary manner by admixing a solution of the compounds with the general chemical formula I with the equivalent amount or an excess of a base or acid, which may be present in solution, where appropriate separating off the precipitate or working up the solution in the customary manner.

The resulting compounds of the formula (I) are optionally reacted with the corresponding (i) solvents and/or (ii) bases or acids to give their solvates, salts and/or solvates of the salts.

The radical definitions given above in general terms or given in preferred ranges are applicable both for the end products of the formula (I) and also correspondingly for the starting materials or intermediates required in each case for the preparation.

The compounds according to the invention exhibit an unforeseeable, valuable pharmacological, pharmacokinetic and pharmacodynamic efficacy profile.

They are therefore suitable for use as medicaments for the treatment and/or prophylaxis of diseases in humans and animals.

The pharmaceutical effectiveness of the compounds according to the invention can be explained by their effect as progesterone receptor antagonists, i.e. their antagonising effect on the progesterone receptor.

The present invention further provides the use of the compounds according to the invention for the treatment and/or prophylaxis of diseases based on hormone-dependent hyperproliferative processes, preferably of gynaecological disorders, in particular of uterus fibroids, endometriosis or hormone-dependent breast cancers.

The present invention further provides the use of the compounds according to the invention for the treatment and/or prophylaxis of diseases, in particular the aforementioned diseases.

The present invention further provides the compounds according to the invention for use in a method for the treatment and/or prophylaxis of uterus fibroids, endometriosis and hormone-dependent breast cancers.

The present invention further provides the use of the compounds according to the invention for producing a medicament for the treatment and/or prophylaxis of diseases, in particular of the aforementioned diseases.

The present invention further provides a method for the treatment and/or prophylaxis of diseases, in particular the aforementioned diseases, using 0.1-100 mg of the compounds according to the invention per day and patient in the case of the treatment of uterus fibroids or endometriosis and for contraceptive use, or of 0.1-500 mg of the compounds according to the invention per day and patient in the case of tumour diseases (e.g. menginiomas or hormone-dependent tumours such as e.g. breast cancer) and in the case of emergency contraception.

The present invention further provides medicaments comprising at least one compound according to the invention and at least one or more further active ingredient, in particular for the treatment and/or prophylaxis of the diseases specified above.

For the treatment of tumour disorders, e.g. the following active ingredients/active ingredient classes can be administered either simultaneously or sequentially: SERMs, SERDs, antioestrogens, aromatase inhibitors, kinase inhibitors, angiogenesis inhibitors and/or cytostatics.

For the treatment of uterus fibroids or endometriosis, the compounds according to the invention can be combined simultaneously or sequentially with gestagens or combinations of oestragens and gestagens.

WO 96/15794 (Spicer et al., Balance Pharm. Inc.), WO 96/03130 (Stockemann et al., Schering AG) and PCT/EP2009/003249 (Moller et al., Bayer Schering Pharma AG) disclose progesterone receptor antagonists/gestagen regimes. Of good suitability for the treatment of uterus fibroids and endometriosis are—optionally repeating—regimes in which the progesterone receptor antagonist is given over a period of two to four months, followed by the administration of the gestagen over a period of one to four weeks. Of particularly good suitability is the—optionally repeating—84-day administration of the progesterone receptor antagonist followed by the 14-day administration of the gestagen.

For the treatment of troubles associated with the menopause, a simultaneous or sequential administration of the compounds according to the invention e.g. with SERMs, SERDs and oestrogens is suitable.

SERMs (Selective Estrogen Receptor Modulators) are those compounds which tissue-selectively have either an antioestrogenic or oestrogenic effect, for example inhibit the effect of oestrogen in the uterus, but have a neutral effect or an effect similar to oestrogen in the bone. Examples are clomifen, raloxifen, tamoxifen, torimifen, bazedoxifen, lasofoxifen and ormeloxifen.

Selective oestrogen receptor destabilizers (SERD) are medicaments which completely antagonise the oestrogen receptor ("pure antioestrogens" without oestrogenic active component) and lead to a degradation of the receptor (for example fulvestrant, ZK-703 and ZK-253 Hoffmann J et al., J Natl Cancer Inst 2004, 96:210-218) and also compounds described in WO 98/007740, WO 99/33855 and WO 03/045972.

Antioestrogens are compounds which completely antagonise the oestrogen receptor, for example fulvestrant.

Aromatase inhibitors inhibit the enzyme aromatase and thus the aromatisation of androgens in oestrogens. These include, inter alia, anastrozole, letrozole, exemestane, vorozole, formestane and fadrozole.

Kinase inhibitors are enzymes which transfer a phosphate radical from ATP to other substrates, there in particular to hydroxy groups, e.g. sorafenib (Nexavar) or imatinib (Gleevec).

Angiogenesis inhibitors, e.g. avastin, reduce and/or block the vascular supply and thus perfusion of a tumour.

Cytostatics, e.g. cis-platin, taxol, taxotere are natural or synthetic substances which inhibit cell growth and/or cell division.

Within the context of the present invention, gestagens are understood as meaning either the natural progesterone itself or synthetic derivatives which, like progesterone itself, bind to the progesterone receptor and, in dosages above the ovulation inhibitory dose, inhibit ovulation. Examples of the synthetic derivatives which may be mentioned are drospirenone, gestodene, levonorgestrel, cyproterone acetate, desogestrel and 3-ketodesogestrel, norethisterone, norethisterone acetate and dienogest.

Combinations of gestagens and oestrogens are the active ingredient combinations which are present in the oral contraceptive known per se, for example Yasmin, Femovan, Triquilar, Marvelon, YAZ etc.

The compounds according to the invention can be systemically and/or locally active. For this purpose, they can be applied in a suitable way, such as e.g. orally, intrauterine (intrauterinary), intravaginally, parenterally, pulmonally, nasally, sublingually, lingually, buccally, rectally, dermally, transdermally, conjunctivally, otically or as an implant or stent.

Intrauterine (intrauterinary) here means in particular application by means of IUS (intrauterine system) or IUD (intrauterine device). The intravaginal application can take place inter alia by means of IVRNRS (intra-vaginal ring/vaginal ring system).

Intrauterine or intravaginal application forms (cf. e.g. WO 01/47490, in particular page 1, line 10 to page 5, line 13 and page 7, line 19 to page 58, line 6, or for vaginal rings: WO 06/010097, in particular page 10, line 22 to page 14, line 28) can comprise the compounds according to the invention and non-silicone and/or silicone polymers, in particular also siloxane-based elastomers (cf. WO 01/47490, in particular page 7, line 19-page 15, line 15).

For these application routes, the compounds according to the invention can be administered in suitable application forms.

Of suitability for oral application are application forms that function according to the prior art and release the compounds according to the invention rapidly and/or in modified manner and which comprise the compounds according to the invention in crystalline and/or amorphised and/or dissolved form, such as e.g. tablets (noncoated or coated tablets, for example with enteric coatings or coatings that are insoluble or have delayed dissolution which control the release of the compound according to the invention), tablets that disintegrate rapidly in the oral cavity, or films/oblates, films/lyophilisates, capsules (for example hard or soft gelatine capsules), sugar-coated tablets, granules, pellets, powders, emulsions, suspensions, aerosols or solutions.

Parenteral application can take place by circumventing an absorption step (e.g. intravenously, intraarterially, intracardially, intraspinally or intralumbally) or with the switching on of an absorption (e.g. intramuscularly, subcutaneously, intracutaneously, percutaneously or intraperitoneally). Application forms suitable for parenteral application are, inter alia, injection and infusion preparations in the form of solutions, suspensions, emulsions, lyophilisates or sterile powders.

Of suitability for the other application routes are e.g. inhalation medicaments (inter alia powder inhalers, nebulisers), nasal drops, solutions, sprays; tablets to be applied lingually, sublingually or bucally, films/oblates or capsules, suppositories, ear or eye preparations, vaginal capsules, aqueous suspensions (lotions, shaking mixtures), lipophilic suspensions, ointments, creams, transdermal therapeutic systems (such as, for example, plasters), milk, pastes, foams, powders for sprinkling, implants or stents.

The compounds according to the invention can be converted to the application forms listed. This can take place in a manner known per se by mixing with inert, nontoxic, pharmaceutically suitable auxiliaries. These auxiliaries include, inter alia, carriers (for example microcrystalline cellulose, lactose, mannitol), solvents (e.g. liquid polyethylene glycols), emulsifiers and dispersants or wetting agents (for example sodium dodecyl sulphate, polyoxysorbitan oleate), binders (for example polyvinylpyrrolidone), synthetic and natural polymers (for example albumin), stabilizers (e.g. antioxidants such as, for example, ascorbic acid), dyes (e.g. inorganic pigments such as, for example, iron oxides) and flavour and/or taste correctors.

The present invention further provides medicaments which comprise at least one compound according to the invention, usually together with one or more inert, nontoxic, pharmaceutically suitable auxiliaries, and their use for the purposes specified above. Nevertheless, it may optionally be necessary to deviate from the stated amounts, specifically depending on bodyweight, application route, individual reaction to the active ingredient, type of preparation and time or interval at which application takes place. Thus, in some cases, it may be sufficient to make do with less than the aforementioned minimum amount whereas in other cases the stated upper limit will need to be exceeded. When administering relatively large amounts, it may be advisable to divide these into two or more individual doses over the day.

Unless stated otherwise, the percentages in the following tests and examples are percentages by weight; parts are parts by weight. Solvent ratios, dilution ratios and concentration data of liquid/liquid solutions refer in each case to the volume.

The examples below serve to illustrate the invention without limiting it in any way.

EXAMPLE 1

(11β,17β)-11-{4-[(Dimethylamino)methyl]phenyl}-17-hydroxy-17-(pentafluoroethyl)estra-4,9-dien-3-one

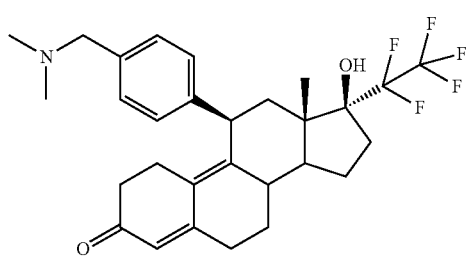 [SMILES: CN(C)Cc1ccc([C@H]2C[C@@]3(C)C(CC[C@@]3(O)C(F)(F)C(F)(F)F)C3CCC4=CC(=O)CCC4=C32)cc1]

a) (5'R,8'S,10'R,13'S,14'S,17'S)-5,5,13'-Trimethyl-17'-(pentafluoroethyl)-1',2',7',8',12',13',14',15',16',17'-decahydro-6'H-spiro[1,3-dioxan-2,3'-[5,10]epoxycyclopenta[a]phenanthren]-17'-ol

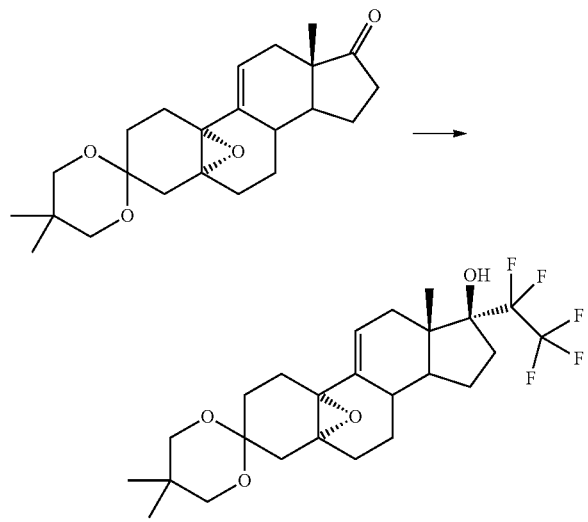

At −70° C., 50 g of (5'R,8'S,10'R,13'S,14'S)-5,5,13'-trimethyl-1',2',6',7',8',12',13',14',15',16'-decahydro-17'H-spiro[1,3-dioxan-2,3'-[5,10]epoxycyclopenta[a]phenanthren]-17'-one (preparation see *Tetrahedron Lett.* 26, 2069-2072 (1985)) were added to 116 g of condensed pentafluoroiodoethane in 500 ml of absolute toluene. 290 ml of a 1.5 molar solution of methyllithium-lithium bromide complex in diethyl ether were added thereto at the same temperature. After-stirring was then carried out for one hour at 0° C. The reaction mixture was then added to saturated aqueous ammonium chloride solution and extracted with ethyl acetate. The organic phase was washed with saturated aqueous sodium chloride solution, dried over sodium sulphate and concentrated by evaporation in vacuo. The crude product was dissolved in 200 ml of acetone and admixed with 450 ml of water. The precipitated product was filtered off and dried in vacuo.

Yield 61.6 g $^1$H-NMR (400 MHz, CDCl$_3$): δ=6.04 brd (1H); 3.60 d (1H); 3.35-3.50 m (3H); 2.51 dbr (1H); 1.06 s (3H); 0.93 s (3H); 0.85 s (3H).

1b) (5R,8S,11R,13S,14S,17S)-11-[4-(Dimethoxymethyl)phenyl]-5',5',13-trimethyl-17-(pentafluoroethyl)-1,2,6,7,8,11,12,13,14,15,16,17-dodecahydrospiro[cyclopenta[a]phenanthren-3,2'-[1,3]dioxane]-5,17(4H)-diol

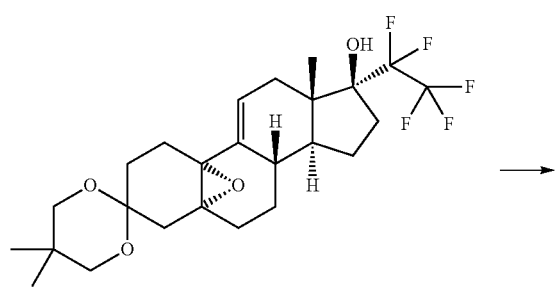

1.48 g of magnesium filings were suspended in 5 ml of THF and admixed with 50 µl of dibromoethane with stirring. At 40° C., a solution of 10.18 ml of 1-bromo-4-(dimethoxymethyl)benzene in 70 ml of THF was added to the suspension and then the mixture was after-stirred for one hour at 50° C. The resulting solution was then cooled to 0° C. 40 mg of CuCl were added and the mixture was after-stirred for a further 15 minutes at 0° C. Then, a solution of 5 g of the substance described under Example 1a) in 50 ml of THF was added. The reaction mixture was then left to come to 23° C. with stirring over ca. 3 hours and then after-stirred at this temperature for 10 hours. Saturated aqueous NH$_4$Cl solution was then added to the reaction mixture with external cooling. The mixture was after-stirred for a further 30 minutes and then extracted several times with ethyl acetate. The combined organic phases were washed with saturated sodium chloride solution and dried over sodium sulphate. The crude product was purified by chromatography over silica gel. This gave 6.4 g of the title compound.

$^1$H-NMR (400 MHz, CDCl$_3$): δ=7.32 d (2H); 7.21 d (2H); 5.36 s (1H); 4.43 s (1H); 4.32 dbr (1H); 3.39-3.58 m (4H); 3.31 s (6H); 1.03 s (3H); 0.86 s (3H); 0.51 s (3H).

c) 4-[(11β,17β)-17-Hydroxy-3-oxo-17-(pentafluoroethyl)estra-4,9-dien-11-yl]benzaldehyde

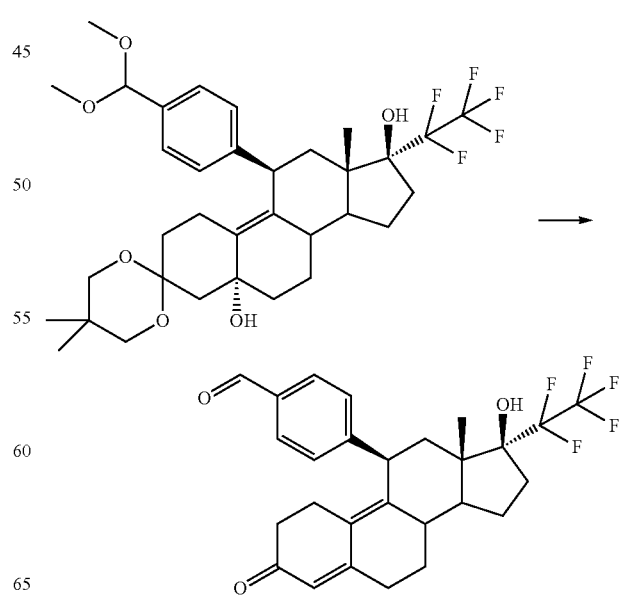

3.5 g of the compound described under 1b) were dissolved in 55 ml of 70% strength acetic acid. The mixture was after-stirred for 16 hours at 30° C. The reaction mixture was then poured onto water and after-stirred for a further 5 hours. It was then filtered. The residue was washed with water, dried and purified by chromatography over silica gel. This gave 2.2 g of the title compound.

$^1$H-NMR (300 MHz, CDCl$_3$): δ=9.99 s (1H); 7.80 d (2H); 7.37 d (2H); 5.80 sbr (1H); 4.51 dbr (1H); 0.58 s (3H).

d) (11β,17β)-11-{4-[(Dimethylamino)methyl]phenyl}-17-hydroxy-17-(pentafluoroethyl)estra-4,9-dien-3-one

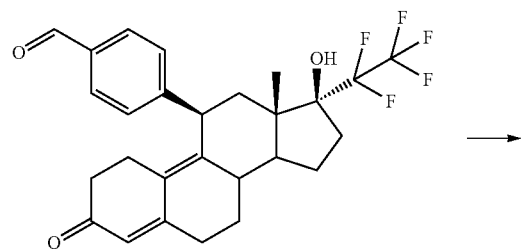

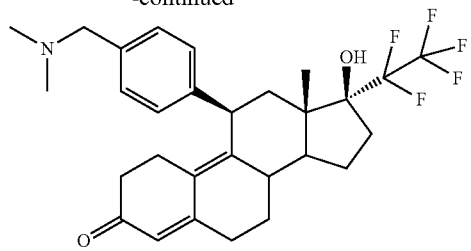

0.4 ml of a 2 molar solution of dimethylamine in THF was added to a solution of 200 mg of the compound described under 1c) in 3 ml of dichloromethane. The mixture was after-stirred for 15 minutes at 23° C. and then 171 mg of sodium triacetoxyborohydride were added. The mixture was then after-stirred for 20 hours at 23° C. The reaction mixture was then poured onto saturated aqueous sodium hydrogencarbonate solution. Extraction was carried out several times with dichloromethane. The combined organic phases were washed with saturated aqueous sodium chloride solution, dried over sodium sulphate and concentrated by evaporation in vacuo. The crude product was purified by chromatography over silica gel. This gave 131 mg of the title compound.

$^1$H-NMR (400 MHz, CDCl$_3$): δ=7.30 d (2H); 7.11 d (2H); 5.78 sbr (1H); 4.44 dbr (1H); 3.32-3.44 m (2H); 2.75 m (1H); 0.58 s (3H).

Examples 2-9 were synthesized analogously to Example 1 from the compound described under 1c) and the respective amine:

| Ex. | Structure | Name | $^1$H-NMR |
|---|---|---|---|
| 2 | 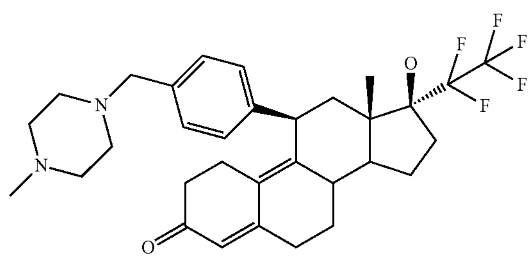 [SMILES: CN1CCN(Cc2ccc([C@H]3C[C@@]4(C)C(CC[C@@]4(O)C(F)(F)C(F)(F)F)C4CCC5=CC(=O)CCC5=C43)cc2)CC1] | (11β,17β)-17-Hydroxy-11-{4-[(4-methylpiperazin-1-yl)methyl]phenyl}-17-(pentafluoroethyl)estra-4,9-dien-3-one | $^1$H-NMR (300 MHz, CDCl$_3$): δ = 7.30 d (2H); 7.10 d (2H); 5.77 sbr (1H); 4.44 dbr (1H); 3.46 m (2H); 2.73 m (1H); 2.27 s (3H); 0.59 s (3H). |
| 3 | 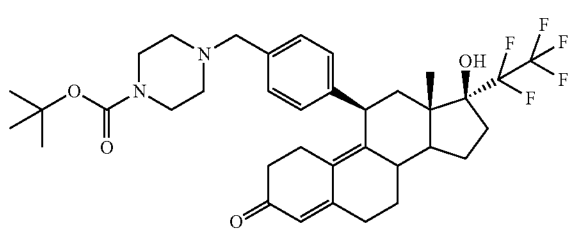 [SMILES: CC(C)(C)OC(=O)N1CCN(Cc2ccc([C@H]3C[C@@]4(C)C(CC[C@@]4(O)C(F)(F)C(F)(F)F)C4CCC5=CC(=O)CCC5=C43)cc2)CC1] | tert-Butyl 4-{4-[(11β,17β)-17-hydroxy-3-oxo-17-(pentafluoroethyl)estra-4,9-dien-11-yl]benzyl}piperazine-1-carboxylate | $^1$H-NMR (300 MHz, CDCl$_3$): δ = 7.20 d (2H); 7.11 d (2H); 5.77 sbr (1H); 4.44 dbr (1H); 3.35-3.47 m (10 H); 1.46 s (9H); 0.58 s (3H). |
| 4 | 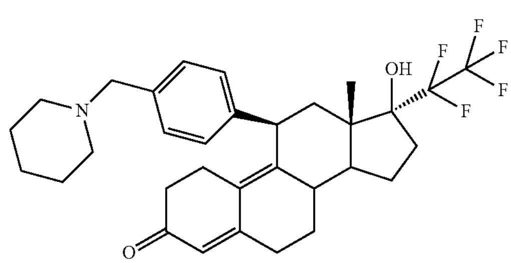 [SMILES: C[C@]12C[C@H](c3ccc(CN4CCCCC4)cc3)C3=C4CCC(=O)C=C4CCC3C1CC[C@@]2(O)C(F)(F)C(F)(F)F] | (11β,17β)-17-Hydroxy-17-(pentafluoroethyl)-11-[4-(piperidin-1-ylmethyl)phenyl]estra-4,9-dien-3-one | $^1$H-NMR (400 MHz, CDCl$_3$): δ = 7.21 d (2H); 7.09 d (2H); 5.78 sbr (1H); 4.44 dbr (1H); 3.42 m (2H); 2.73 m (1H); 0.59 s (3H). |

-continued

| Ex. | Structure | Name | $^1$H-NMR |
|---|---|---|---|
| 5 | 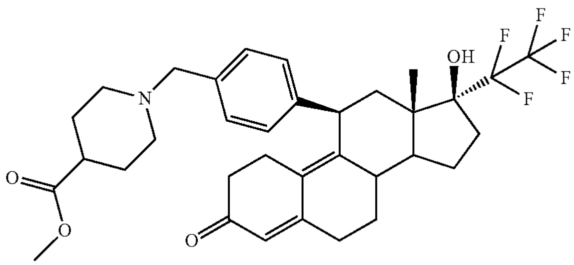 [SMILES: COC(=O)C1CCN(Cc2ccc([C@H]3C[C@@]4(C)C(CC[C@@]4(O)C(F)(F)C(F)(F)F)C4CCC5=CC(=O)CCC5=C43)cc2)CC1] | Methyl 1-{4-[(11β,17β)-17-hydroxy-3-oxo-17-(pentafluoroethyl)estra-4,9-dien-11-yl]benzyl}piperidine-4-carboxylate | $^1$H-NMR (400 MHz, CDCl$_3$): δ = 7.18 d (2H); 7.10 d (2H); 5.78 sbr (1H); 4.45 dbr (1H); 3.67 m (5H); 3.43 m (2H); 2.70-2.90 m (4H); 0.60 s (3H). |
| 6 | 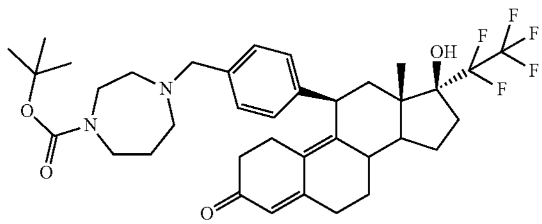 [SMILES: CC(C)(C)OC(=O)N1CCCN(Cc2ccc([C@H]3C[C@@]4(C)C(CC[C@@]4(O)C(F)(F)C(F)(F)F)C4CCC5=CC(=O)CCC5=C43)cc2)CC1] | tert-Butyl 4-{4-[(11β,17β)-17-hydroxy-3-oxo-17-(pentafluoroethyl)estra-4,9-dien-11-yl]benzyl}-1,4-diazepane-1-carboxylate | $^1$H-NMR (400 MHz, CDCl$_3$): δ = 7.21 d (2H); 7.10 d (2H); 5.78 sbr (1H); 4.44 dbr (1H); 3.58 m (2H); 3.38-3.53 m (5H); 2.73 m (1H); 2.50-2.68 m (8H); 1.48 s (9H); 0.58 s (3H). |
| 7 | 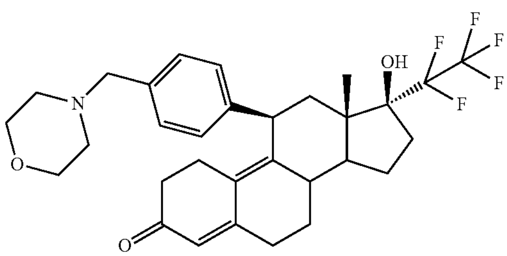 [SMILES: C[C@]12C[C@H](c3ccc(CN4CCOCC4)cc3)C3=C4CCC(=O)C=C4CCC3C1CC[C@@]2(O)C(F)(F)C(F)(F)F] | (11β,17β)-17-Hydroxy-11-[4-(morpholin-4-ylmethyl)phenyl]-17-(pentafluoroethyl)estra-4,9-dien-3-one | $^1$H-NMR (300 MHz, CDCl$_3$): δ = 7.21 d (2H); 7.11 d (2H); 5.77 sbr (1H); 4.44 dbr (1H); 3.62-3.76 m (4H); 3.45 m (2H); 2.72 m (1H); 2.48-2.68 m (3H); 0.59 s (3H). |
| 8 | 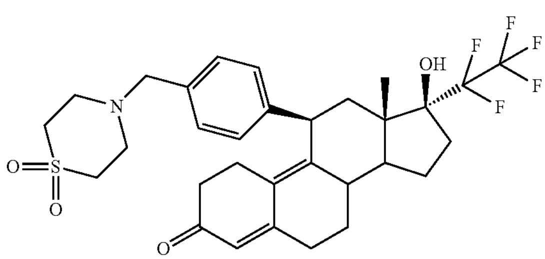 [SMILES: C[C@]12C[C@H](c3ccc(CN4CCS(=O)(=O)CC4)cc3)C3=C4CCC(=O)C=C4CCC3C1CC[C@@]2(O)C(F)(F)C(F)(F)F] | (11β,17β)-11-{4-[(1,1-Dioxidothiomorpholin-4-yl)methyl]phenyl}-17-hydroxy-17-(pentafluoroethyl)estra-4,9-dien-3-one | $^1$H-NMR (300 MHz, CDCl$_3$): δ = 7.20 d (2H); 7.13 d (2H); 5.78 sbr (1H); 4.45 dbr (1H); 3.61 m (2H); 3.05 m (4H); 2.96 m (4H); 2.73 m (1H); 0.59 s (3H). |
| 9 | 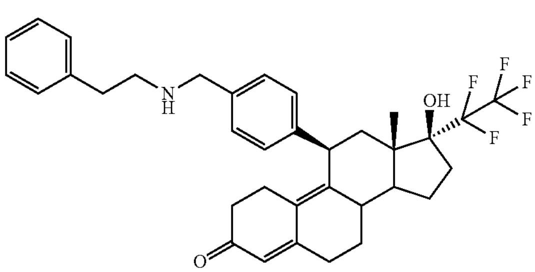 [SMILES: C[C@]12C[C@H](c3ccc(CNCCc4ccccc4)cc3)C3=C4CCC(=O)C=C4CCC3C1CC[C@@]2(O)C(F)(F)C(F)(F)F] | (11β,17β)-17-Hydroxy-17-(pentafluoroethyl)-11-(4-{[(2-phenylethyl)amino]methyl}phenyl)estra-4,9-dien-3-one | $^1$H-NMR (400 MHz, CDCl$_3$): δ = 7.27 d (2H); 7.18 m (5H); 7.09 d (2H); 5.78 sbr (1H); 4.43 dbr (1H); 3.76 m (2H); 2.92 m (2H); 2.83 m (2H); 2.71 m (1H); 0.58 s (3H). |

EXAMPLE 10

(11β,17β)-17-Hydroxy-17-(pentafluoroethyl)-11-[4-(piperazin-1-yl-methyl)phenyl]estra-4,9-dien-3-one

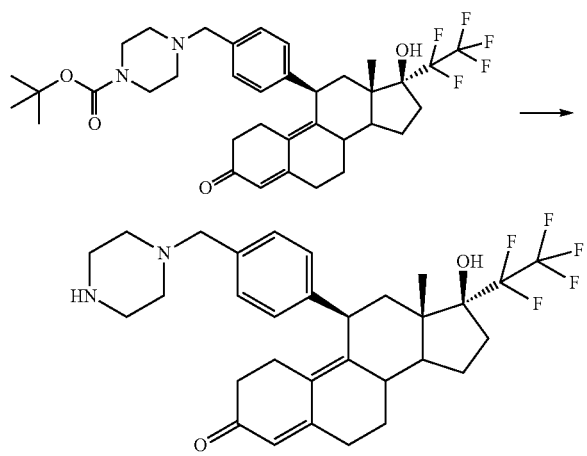

0.5 ml of trifluoroacetic acid was added to a solution of 180 mg of the compound described under Example 3 in 3 ml of dichloromethane. The reaction mixture was after-stirred for 40 minutes at 23° C. and then poured onto saturated aqueous sodium hydrogencarbonate solution. The mixture was then after-stirred for a further 30 minutes and then extracted several times with dichloromethane. The combined organic phases were washed with saturated aqueous sodium chloride solution, dried over sodium sulphate and concentrated by evaporation in vacuo. The crude product was purified by chromatography over silica gel. This gave 87 mg of the title compound.

$^1$H-NMR (400 MHz, CDCl$_3$): δ=7.20 d (2H); 7.10 d (2H); 5.77 sbr (1H); 4.43 dbr (1H); 3.38-3.52 m (2H); 2.80-2.92 m (4H); 2.72 m (1H); 0.58 s (3H).

EXAMPLE 11

(11β,17β)-11-{4-[(4-Acetylpiperazin-1-yl)methyl]phenyl}-17-hydroxy-17-(pentafluoroethyl)estra-4,9-dien-3-one

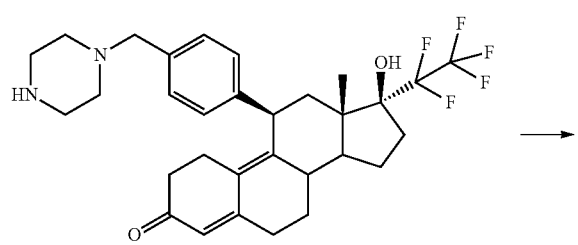

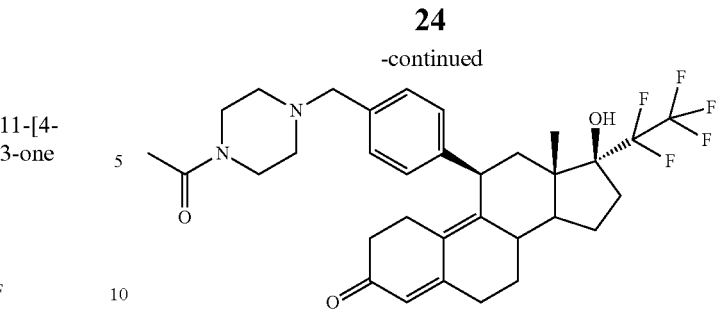

0.4 ml of triethylamine was added to a solution of 80 mg of the compound described under Example 10 in 2.5 ml of dichloromethane. The mixture was cooled to 0° C. and 14 μl of acetic anhydride were added. The mixture was then left to come to 23° C. and after-stirred for 1 hour. The reaction mixture was then poured onto saturated aqueous sodium hydrogen-carbonate solution. The mixture was after-stirred for a further 30 minutes and then extracted several times with dichloromethane. The combined organic phases were washed with saturated aqueous sodium chloride solution, dried over sodium sulphate and concentrated by evaporation in vacuo. The crude product was purified by chromatography over silica gel. This gave 80 mg of the title compound.

$^1$H-NMR (400 MHz, CDCl$_3$): δ=7.20 d (2H); 7.12 d (2H); 5.78 sbr (1H); 4.45 dbr (1H); 3.38-3.50 m (4H); 2.75 m (1H); 2.06 s (3H); 0.59 s (3H).

EXAMPLE 12

(11β,17β)-17-Hydroxy-11-(4-{[4-(methylsulphonyl)piperazin-1-yl]methyl}phenyl)-17-(pentafluoroethyl)estra-4,9-dien-3-one

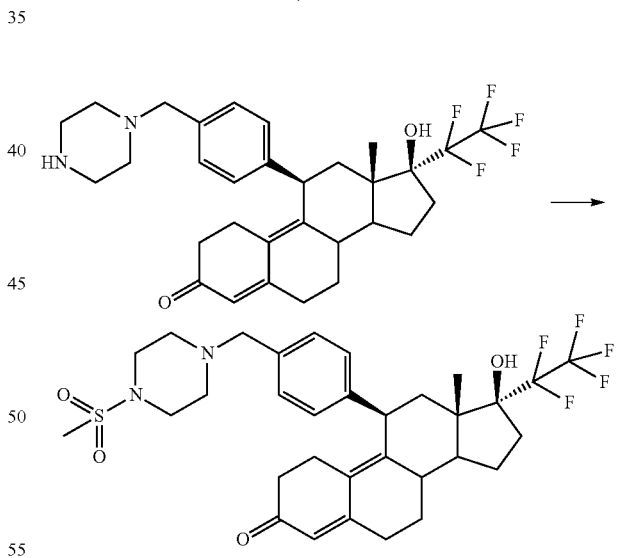

71 μl of triethylamine were added to a solution of 96 mg of the compound described under Example 10 in 3 ml of THF. The mixture was cooled to 0° C. and 20 μl of methanesulphonyl chloride were added. The mixture was then left to reach 23° C. and after-stirred for 1 hour. The reaction mixture was then poured onto saturated aqueous sodium hydrogencarbonate solution. The mixture was after-stirred for a further 30 minutes and then extracted several times with dichloromethane. The combined organic phases were washed with saturated aqueous sodium chloride solution, dried over sodium sulphate and concentrated by evaporation in vacuo.

The crude product was purified by chromatography over silica gel. This gave 82 mg of the title compound.

$^1$H-NMR (300 MHz, CDCl$_3$): δ=7.20 d (2H); 7.13 d (2H); 5.79 sbr (1H); 4.45 dbr (1H); 3.50 m (2H); 3.15-3.35 m (4H); 2.78 s (3H); 0.59 s (3H).

EXAMPLE 13

(11β,17β)-11-{4-[(4-Benzoylpiperazin-1-yl)methyl]phenyl}-17-hydroxy-17-(Pentafluoroethyl)estra-4,9-dien-3-one

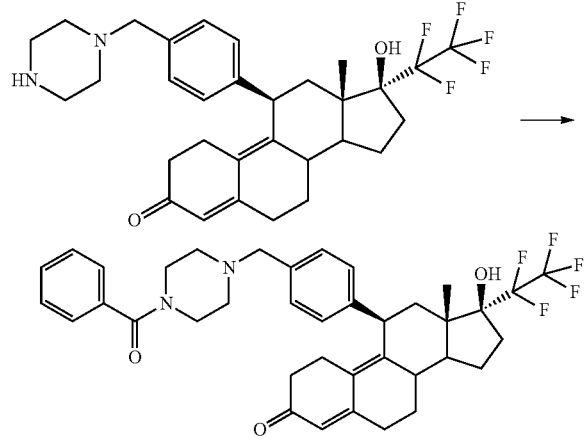

0.22 ml of triethylamine was added to a solution of 300 mg of the compound described under Example 10 in 10 ml of THF. The mixture was cooled to 0° C. and 93 μl of benzoyl chloride were added. The mixture was then left to reach 23° C. and after-stirred for 1 hour. The reaction mixture was then poured onto saturated aqueous sodium hydrogencarbonate solution. It was after-stirred for a further 30 minutes and then extracted several times with dichloromethane. The combined organic phases were washed with saturated aqueous sodium chloride solution, dried over sodium sulphate and concentrated by evaporation in vacuo. The crude product was purified by chromatography over silica gel. This gave 290 mg of the title compound.

$^1$H-NMR (300 MHz, CDCl$_3$): δ=7.33-7.47 m (5H); 7.20 d (2H); 7.11 d (2H); 5.77 sbr (1H); 4.45 dbr (1H); 3.68-3.92 m (2H); 3.49 m (2H); 3.34-3.52 m (2H); 2.73 m (1H); 0.58 s (3H).

EXAMPLE 14

(11β,17β)-11-(4-{[4-(2,2-Dimethylpropanoyl)piperazin-1-yl]methyl}phenyl)-17-hydroxy-17-(pentafluoroethyl)estra-4,9-dien-3-one

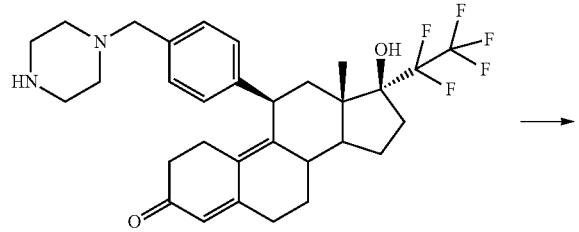

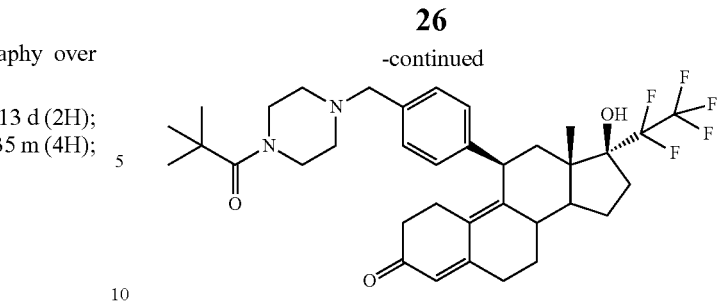

0.22 ml of triethylamine was added to a solution of 300 mg of the compound described under Example 10 in 10 ml of THF. The mixture was cooled to 0° C. and 98 μl of pivaloyl chloride were added. The mixture was then left to reach 23° C. and after-stirred for 1 hour. The reaction mixture was then poured onto saturated aqueous sodium hydrogencarbonate solution. The mixture was after-stirred for a further 30 minutes and then extracted several times with dichloromethane. The combined organic phases were washed with saturated aqueous sodium chloride solution, dried over sodium sulphate and concentrated by evaporation in vacuo. The crude product was purified by chromatography over silica gel. This gave 241 mg of the title compound.

$^1$H-NMR (300 MHz, CDCl$_3$): δ=7.21 d (2H); 7.11 d (2H); 5.78 sbr (1H); 4.43 dbr (1H); 3.55-3.70 m (4H); 3.46 m (2H); 2.74 m (1H); 1.25 s (9H); 0.59 s (3H).

EXAMPLE 15

1-{4-[(11β,17β)-17-Hydroxy-3-oxo-17-(pentafluoroethyl)estra-4,9-dien-11-yl]benzyl}piperidine-4-carboxylic acid

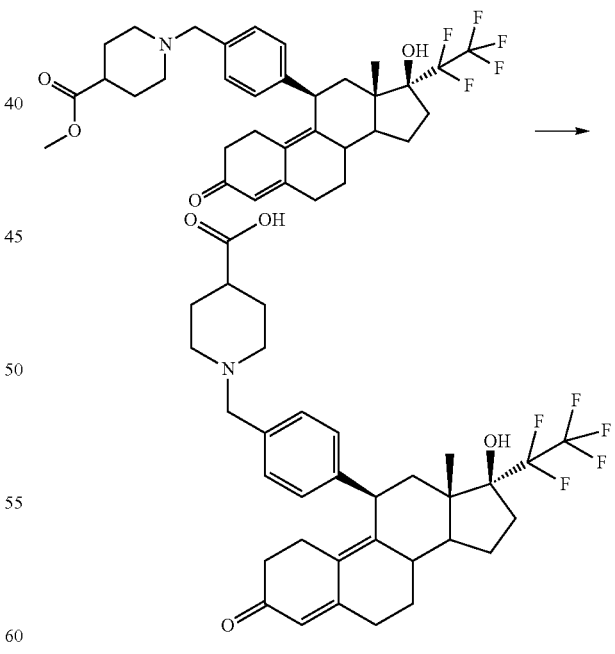

0.52 ml of a 2 molar aqueous sodium hydroxide solution was added to a solution of 200 mg of the compound described under Example 5 in 5 ml of methanol. The reaction mixture is after-stirred for 48 hours at 23° C. and then diluted with 5 ml of water. It was then cooled to 0° C. and acidified by adding 0.15 ml of 2 normal hydrochloric acid. The precipitated product was filtered off, dried and purified by chromatography over silica gel. This gave 50 mg of the title compound.

¹H-NMR (400 MHz, CDCl₃): 1δ=7.25 d (2H); 7.14 d (2H); 5.74 sbr (1H); 4.40 dbr (1H); 3.83 d (2H); 3.70 d (2H); 2.90-3.21 m (2H); 2.70 m (1H); 1.25 s (9H); 0.58 s (3H).

EXAMPLE 16

(11β,17β)-11-[4-(1,4-Diazepan-1-ylmethyl)phenyl]-17-hydroxy-17-(pentafluoroethyl)estra-4,9-dien-3-one

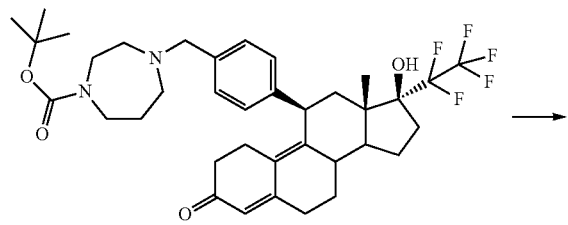

63 mg of the title compound were obtained analogously to Example 10 from 170 mg of the compound described under Example 6 by reaction with trifluoroacetic acid in dichloromethane.

¹H-NMR (400 MHz, CDCl₃): δ=7.22 d (2H); 7.10 d (2H); 5.78 sbr (1H); 4.43 dbr (1H); 3.60 m (2H); 0.57 s (3H).

EXAMPLE 17

(11β,17β)-11-{4-[(4-Acetyl-1,4-diazepan-1-yl)methyl]phenyl}-17-hydroxy-17-(pentafluoroethyl)estra-4,9-dien-3-one

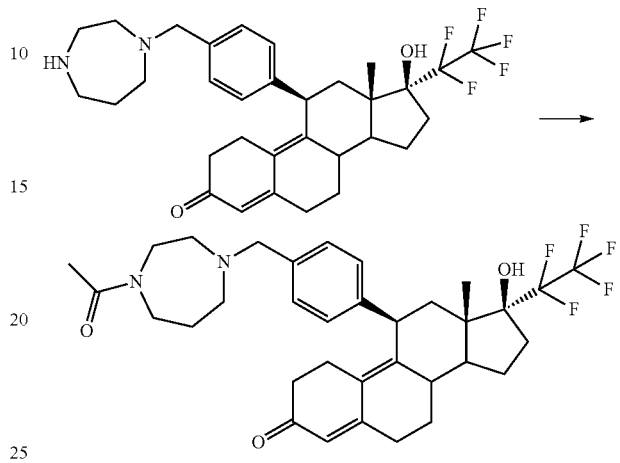

27 mg of the title compound were prepared analogously to Example 11 from 45 mg of the compound described under Example 16 by reaction with acetic anhydride in dichloromethane.

¹H-NMR (300 MHz, CDCl₃): δ=7.21 d (2H); 7.11 d (2H); 5.79 sbr (1H); 4.42 dbr (1H); 3.55-3.70 m (4H); 3.42-3.55 m (2H); 2.75 m (1H); 2.10 s (3H); 0.57 s (3H).

Examples 18-54 were prepared according to the following procedure by parallel synthesis: 0.6 ml of a 0.67 molar suspension of sodium triacetoxyborohydride in 1,2-dichloroethane was introduced as initial charge. 0.4 ml of a 0.5 molar solution of the compound described under 1c) in 1,2-dichloroethane, and then 0.5 ml of a 0.5 molar solution of the respective amine in THF were added. After-stirring was then carried out for 12 hours at 50° C. The reaction mixture was then admixed with 2.5 ml of ethyl acetate and 1.5 ml of a 10% strength aqueous sodium hydroxide solution. The organic phase was separated off and concentrated by evaporation. The crude products were purified by HPLC and analyzed by HPLC-MS (Waters Acquity Ultra Performance LC, photo diode array detector wavelength 210-350 nm, column Acquity HPLC BEH C18 1.7 μm, 2.1×50 mm, column temperature 60° C., gradient 1-99% acetonitrile in 0.1% formic acid/water, flow rate 0.8 ml/min., runtime 2 min.).

| Ex. | Structure | Name | HPLC-MS (MH⁺, RT) |
|---|---|---|---|
| 18 | 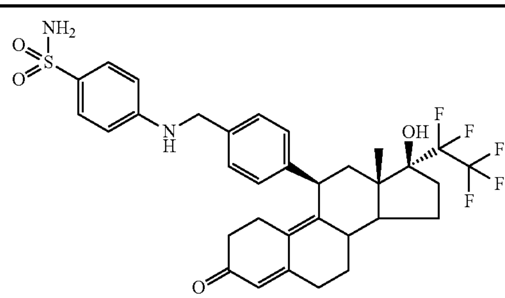 | 4-({4-[(11β,17β)-17-Hydroxy-3-oxo-17-(pentafluoroethyl)estra-4,9-dien-11-yl]benzyl}amino)benzenesulphonamide | 652, 1.30 min. |

-continued

| Ex. | Structure | Name | HPLC-MS (MH+, RT) |
|---|---|---|---|
| 19 | 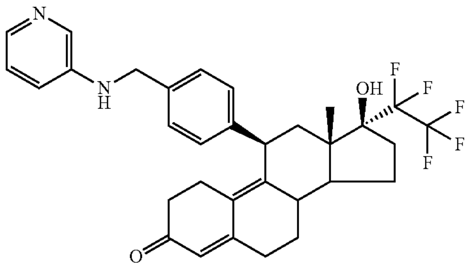 [SMILES: C[C@]12C[C@H](c3ccc(CNc4cccnc4)cc3)C3=C4CCC(=O)C=C4CCC3C1CC[C@@]2(O)C(F)(F)C(F)(F)F] | (11β,17β)-17-Hydroxy-17-(pentafluoroethyl)-11-{4-[(pyridin-3-ylamino)methyl]phenyl}estra-4,9-dien-3-one | 574, 1.04 min. |
| 20 | 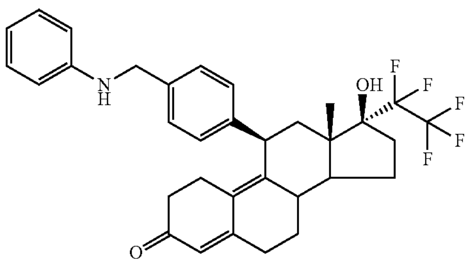 [SMILES: C[C@]12C[C@H](c3ccc(CNc4ccccc4)cc3)C3=C4CCC(=O)C=C4CCC3C1CC[C@@]2(O)C(F)(F)C(F)(F)F] | (11β,17β)-11-[4-(Anilinomethyl)phenyl]-17-hydroxy-17-(pentafluoroethyl)estra-4,9-dien-3-one | 573, 1.48 min. |
| 21 | 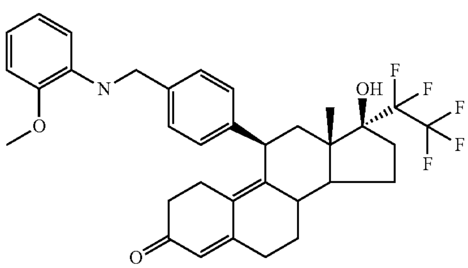 [SMILES: COc1ccccc1NCc1ccc([C@H]2C[C@@]3(C)C(CC[C@@]3(O)C(F)(F)C(F)(F)F)C3CCC4=CC(=O)CCC4=C32)cc1] | (11β,17β)-17-Hydroxy-11-(4-{[(2-methoxyphenyl)amino]methyl}phenyl)-17-(pentafluoroethyl)estra-4,9-dien-3-one | 603, 1.51 min. |
| 22 | 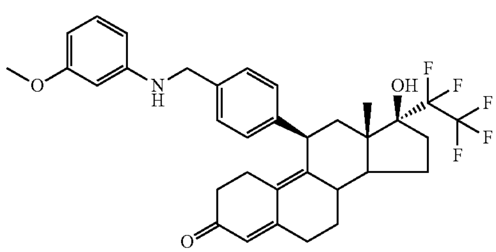 [SMILES: COc1cccc(NCc2ccc([C@H]3C[C@@]4(C)C(CC[C@@]4(O)C(F)(F)C(F)(F)F)C4CCC5=CC(=O)CCC5=C43)cc2)c1] | (11β,17β)-17-Hydroxy-11-(4-{[(3-methoxyphenyl)amino]methyl}phenyl)-17-(pentafluoroethyl)estra-4,9-dien-3-one | 603, 1.47 min. |
| 23 | 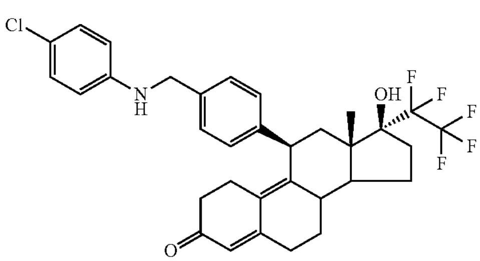 [SMILES: C[C@]12C[C@H](c3ccc(CNc4ccc(Cl)cc4)cc3)C3=C4CCC(=O)C=C4CCC3C1CC[C@@]2(O)C(F)(F)C(F)(F)F] | (11β,17β)-11-(4-{[(4-Chlorophenyl)amino]methyl}phenyl)-17-hydroxy-17-(pentafluoroethyl)estra-4,9-dien-3-one | 607, 1.55 min. |

-continued

| Ex. | Structure | Name | HPLC-MS (MH+, RT) |
|---|---|---|---|
| 24 | 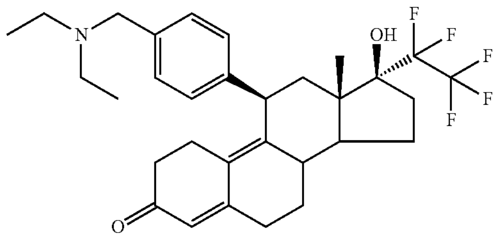 [SMILES: CCN(CC)Cc1ccc([C@H]2C[C@@]3(C)C(CC[C@@]3(O)C(F)(F)C(F)(F)F)C3CCC4=CC(=O)CCC4=C32)cc1] | (11β,17β)-11-{4-[(Diethylamino)methyl]phenyl}-17-hydroxy-17-(pentafluoroethyl)estra-4,9-dien-3-one | 553, 1.02 min. |
| 25 | 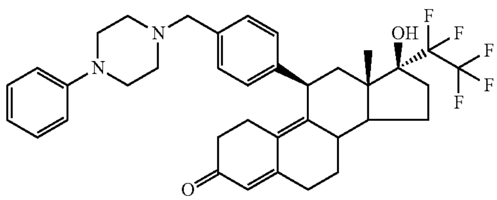 [SMILES: C[C@]12C[C@H](c3ccc(CN4CCN(c5ccccc5)CC4)cc3)C3=C4CCC(=O)C=C4CCC3C1CC[C@@]2(O)C(F)(F)C(F)(F)F] | (11β,17β)-17-Hydroxy-17-(pentafluoroethyl)-11-{4-[(4-phenylpiperazin-1-yl)methyl]phenyl}estra-4,9-dien-3-one | 642, 1.10 min. |
| 26 | 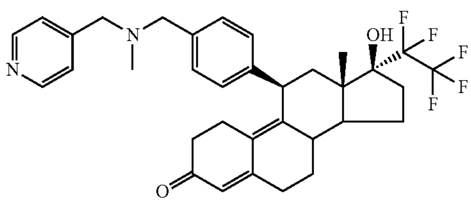 [SMILES: CN(Cc1ccncc1)Cc1ccc([C@H]2C[C@@]3(C)C(CC[C@@]3(O)C(F)(F)C(F)(F)F)C3CCC4=CC(=O)CCC4=C32)cc1] | (11β,17β)-17-Hydroxy-11-(4-{[methyl(pyridin-4-ylmethyl)amino]methyl}phenyl)-17-(pentafluoroethyl)estra-4,9-dien-3-one | 602, 0.99 min. |
| 27 | 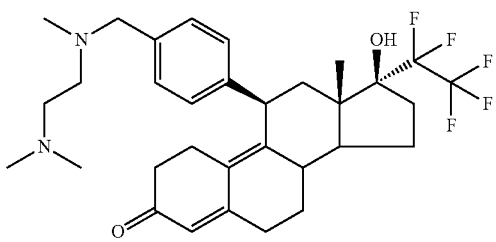 [SMILES: CN(C)CCN(C)Cc1ccc([C@H]2C[C@@]3(C)C(CC[C@@]3(O)C(F)(F)C(F)(F)F)C3CCC4=CC(=O)CCC4=C32)cc1] | (11β,17β)-11-[4-({[2-(Dimethylamino)ethyl](methyl)amino}methyl)phenyl]-17-hydroxy-17-(pentafluoroethyl)estra-4,9-dien-3-one | 582, 0.89 min. |
| 28 | 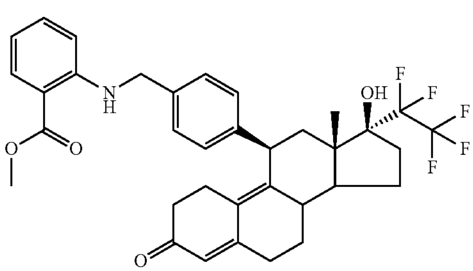 [SMILES: COC(=O)c1ccccc1NCc1ccc([C@H]2C[C@@]3(C)C(CC[C@@]3(O)C(F)(F)C(F)(F)F)C3CCC4=CC(=O)CCC4=C32)cc1] | Methyl 2-({4-[(11β,17β)-17-hydroxy-3-oxo-17-(pentafluoroethyl)estra-4,9-dien-11-yl]benzyl}amino)benzoate | 631, 1.59 min. |
| 29 | 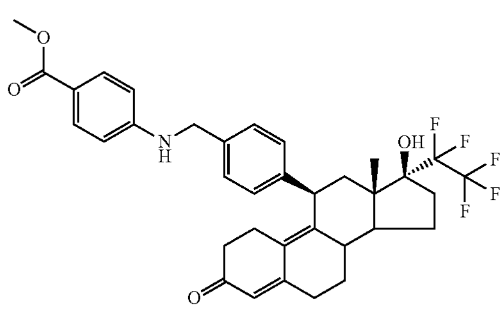 [SMILES: COC(=O)c1ccc(NCc2ccc([C@H]3C[C@@]4(C)C(CC[C@@]4(O)C(F)(F)C(F)(F)F)C4CCC5=CC(=O)CCC5=C43)cc2)cc1] | Methyl 4-({4-[(11β,17β)-17-hydroxy-3-oxo-17-(pentafluoroethyl)estra-4,9-dien-11-yl]benzyl}amino)benzoate | 631, 1.46 min. |

-continued

| Ex. | Structure | Name | HPLC-MS (MH+, RT) |
|---|---|---|---|
| 30 | 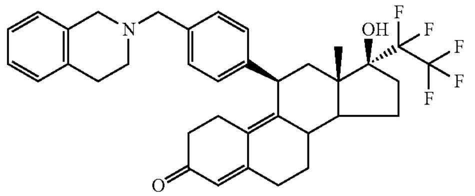 [SMILES: C[C@]12C[C@H](c3ccc(CN4CCc5ccccc5C4)cc3)C3=C4CCC(=O)C=C4CCC3C1CC[C@@]2(O)C(F)(F)C(F)(F)F] | (11β,17β)-11-[4-(3,4-Dihydroisoquinolin-2(1H)-ylmethyl)phenyl]-17-hydroxy-17-(pentafluoroethyl)estra-4,9-dien-3-one | 613, 1.07 min. |
| 31 | 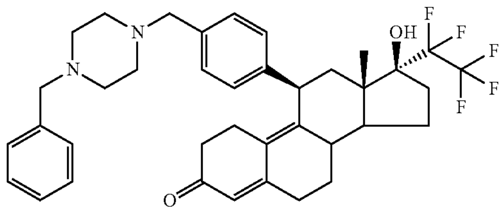 [SMILES: C[C@]12C[C@H](c3ccc(CN4CCN(Cc5ccccc5)CC4)cc3)C3=C4CCC(=O)C=C4CCC3C1CC[C@@]2(O)C(F)(F)C(F)(F)F] | (11β,17β)-11-{4-[(4-Benzylpiperazin-1-yl)methyl]phenyl}-17-hydroxy-17-(pentafluoroethyl)estra-4,9-dien-3-one | 656, 1.09 min. |
| 32 | 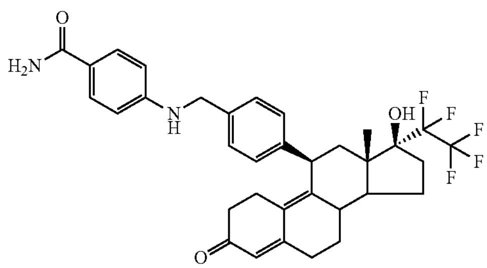 [SMILES: C[C@]12C[C@H](c3ccc(CNc4ccc(C(N)=O)cc4)cc3)C3=C4CCC(=O)C=C4CCC3C1CC[C@@]2(O)C(F)(F)C(F)(F)F] | 4-({4-[(11β,17β)-17-Hydroxy-3-oxo-17-(pentafluoroethyl)estra-4,9-dien-11-yl]benzyl}amino)benzamide | 616, 1.26 min. |
| 33 | 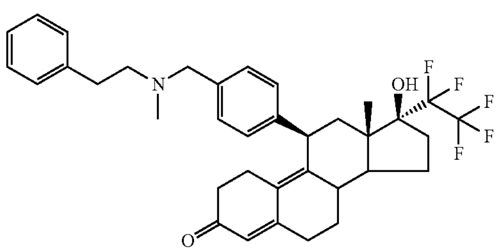 [SMILES: CN(CCc1ccccc1)Cc1ccc([C@H]2C[C@@]3(C)C(CC[C@@]3(O)C(F)(F)C(F)(F)F)C3CCC4=CC(=O)CCC4=C32)cc1] | (11β,17β)-17-Hydroxy-11-(4-{[methyl(2-phenylethyl)amino]methyl}phenyl)-17-(pentafluoroethyl)estra-4,9-dien-3-one | 615, 1.09 min. |
| 34 | 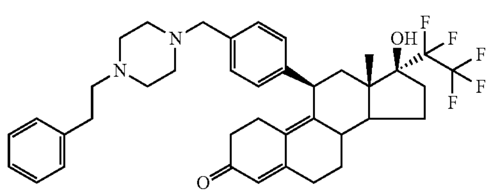 [SMILES: C[C@]12C[C@H](c3ccc(CN4CCN(CCc5ccccc5)CC4)cc3)C3=C4CCC(=O)C=C4CCC3C1CC[C@@]2(O)C(F)(F)C(F)(F)F] | (11β,17β)-17-Hydroxy-17-(pentafluoroethyl)-11-(4-{[4-(2-phenylethyl)piperazin-1-yl]methyl}phenyl)estra-4,9-dien-3-one | 670, 1.10 min. |
| 35 | 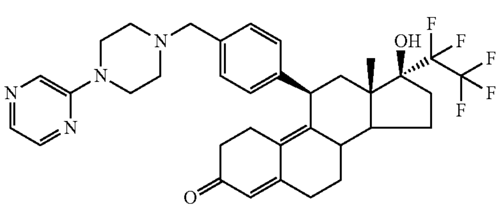 [SMILES: C[C@]12C[C@H](c3ccc(CN4CCN(c5cnccn5)CC4)cc3)C3=C4CCC(=O)C=C4CCC3C1CC[C@@]2(O)C(F)(F)C(F)(F)F] | (11β,17β)-17-Hydroxy-17-(pentafluoroethyl)-11-(4-{[4-(pyrazin-2-yl)piperazin-1-yl]methyl}phenyl)estra-4,9-dien-3-one | 644, 1.02 min. |
| 36 | 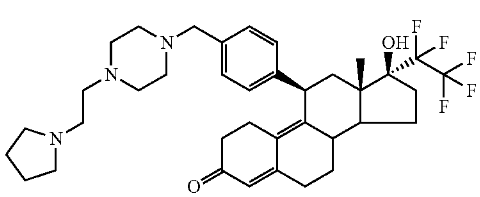 [SMILES: C[C@]12C[C@H](c3ccc(CN4CCN(CCN5CCCC5)CC4)cc3)C3=C4CCC(=O)C=C4CCC3C1CC[C@@]2(O)C(F)(F)C(F)(F)F] | (11β,17β)-17-Hydroxy-17-(pentafluoroethyl)-11-[4-({4-[2-(pyrrolidin-1-yl)ethyl]piperazin-1-yl}methyl)phenyl]estra-4,9-dien-3-one | 663, 0.86 min. |

-continued

| Ex. | Structure | Name | HPLC-MS (MH+, RT) |
|---|---|---|---|
| 37 | 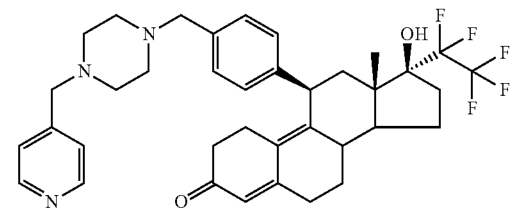 | (11β,17β)-17-Hydroxy-17-(pentafluoroethyl)-11-(4-{[4-(pyridin-4-ylmethyl)piperazin-1-yl]methyl}phenyl)estra-4,9-dien-3-one | 657, 0.88 min. |
| 38 | 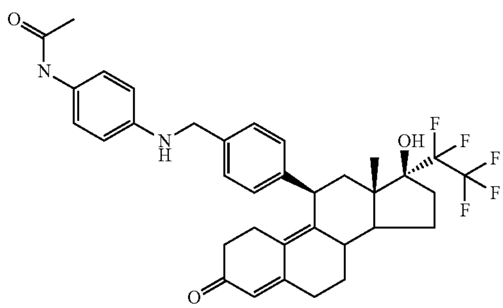 [SMILES: CC(=O)Nc1ccc(NCc2ccc([C@H]3C[C@@]4(C)C(CC[C@@]4(O)C(F)(F)C(F)(F)F)C4CCC5=CC(=O)CCC5=C43)cc2)cc1] | N-[4-({4-[(11β,17β)-17-Hydroxy-3-oxo-17-(pentafluoroethyl)estra-4,9-dien-11-yl]benzyl}amino)phenyl]acetamide | 630, 1.26 min. |
| 39 | 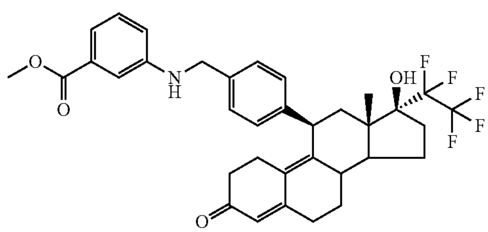 [SMILES: COC(=O)c1cccc(NCc2ccc([C@H]3C[C@@]4(C)C(CC[C@@]4(O)C(F)(F)C(F)(F)F)C4CCC5=CC(=O)CCC5=C43)cc2)c1] | Methyl 3-({4-[(11β,17β)-17-hydroxy-3-oxo-17-(pentafluoroethyl)estra-4,9-dien-11-yl]benzyl}amino)benzoate | 631, 1.48 min. |
| 40 | 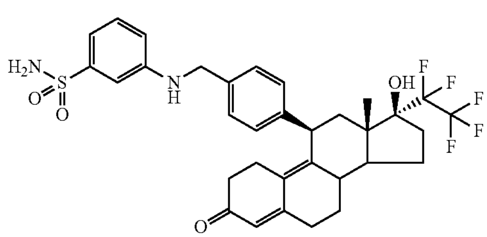 [SMILES: C[C@]12C[C@H](c3ccc(CNc4cccc(S(N)(=O)=O)c4)cc3)C3=C4CCC(=O)C=C4CCC3C1CC[C@@]2(O)C(F)(F)C(F)(F)F] | 3-({4-[(11β,17β)-17-Hydroxy-3-oxo-17-(pentafluoroethyl)estra-4,9-dien-11-yl]benzyl}amino)benzenesulphonamide | 652, 1.31 min. |
| 41 | 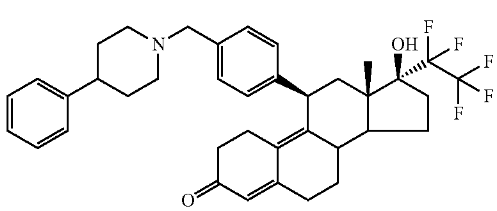 [SMILES: C[C@]12C[C@H](c3ccc(CN4CCC(c5ccccc5)CC4)cc3)C3=C4CCC(=O)C=C4CCC3C1CC[C@@]2(O)C(F)(F)C(F)(F)F] | (11β,17β)-17-Hydroxy-17-(pentafluoroethyl)-11-{4-[(4-phenylpiperidin-1-yl)methyl]phenyl}estra-4,9-dien-3-one | 641, 1.11 min. |
| 42 | 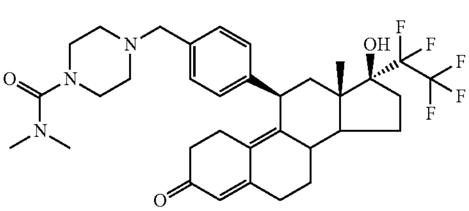 [SMILES: CN(C)C(=O)N1CCN(Cc2ccc([C@H]3C[C@@]4(C)C(CC[C@@]4(O)C(F)(F)C(F)(F)F)C4CCC5=CC(=O)CCC5=C43)cc2)CC1] | 4-{4-[(11β,17β)-17-Hydroxy-3-oxo-17-(pentafluoroethyl)estra-4,9-dien-11-yl]benzyl}-N,N-dimethylpiperazine-1-carboxamide | 637, 1.00 min. |

-continued

| Ex. | Structure | Name | HPLC-MS (MH+, RT) |
|---|---|---|---|
| 43 | 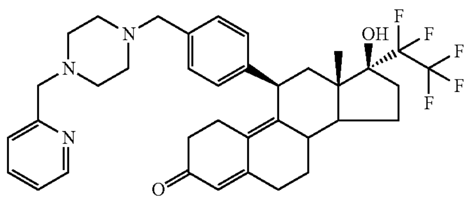 [SMILES: C[C@]12C[C@H](c3ccc(CN4CCN(Cc5ccccn5)CC4)cc3)C3=C4CCC(=O)C=C4CCC3C1CC[C@@]2(O)C(F)(F)C(F)(F)F] | (11β,17β)-17-Hydroxy-17-(pentafluoroethyl)-11-(4-{[4-(pyridin-2-ylmethyl)piperazin-1-yl]methyl}phenyl)estra-4,9-dien-3-one | 657, 0.94 min. |
| 44 | 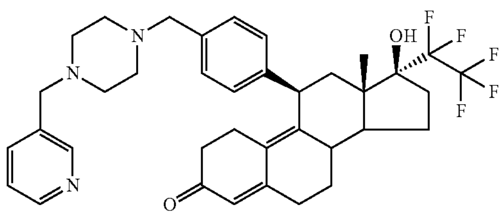 [SMILES: C[C@]12C[C@H](c3ccc(CN4CCN(Cc5cccnc5)CC4)cc3)C3=C4CCC(=O)C=C4CCC3C1CC[C@@]2(O)C(F)(F)C(F)(F)F] | (11β,17β)-17-Hydroxy-17-(pentafluoroethyl)-11-(4-{[4-(pyridin-3-ylmethyl)piperazin-1-yl]methyl}phenyl)estra-4,9-dien-3-one | 657, 0.91 min. |
| 45 | 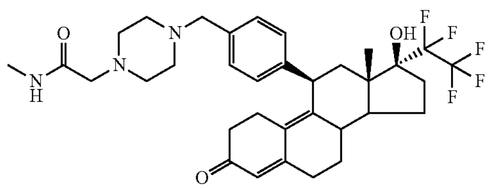 [SMILES: CNC(=O)CN1CCN(Cc2ccc([C@H]3C[C@@]4(C)C(CC[C@@]4(O)C(F)(F)C(F)(F)F)C4CCC5=CC(=O)CCC5=C43)cc2)CC1] | 2-(4-{4-[(11β,17β)-17-Hydroxy-3-oxo-17-(pentafluoroethyl)estra-4,9-dien-11-yl]benzyl}piperazin-1-yl)-N-methylacetamide | 637, 0.97 min. |
| 46 | 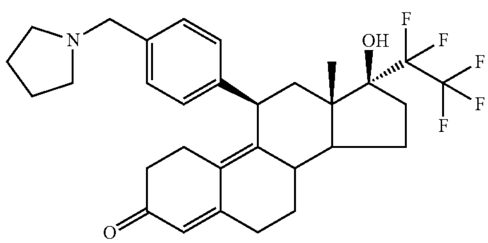 [SMILES: C[C@]12C[C@H](c3ccc(CN4CCCC4)cc3)C3=C4CCC(=O)C=C4CCC3C1CC[C@@]2(O)C(F)(F)C(F)(F)F] | (11β,17β)-17-Hydroxy-17-(pentafluoroethyl)-11-[4-(pyrrolidin-1-ylmethyl)phenyl]estra-4,9-dien-3-one | 551, 1.02 min. |
| 47 | 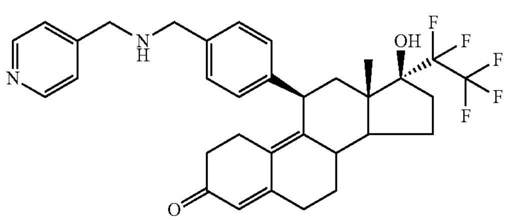 | (11β,17β)-17-Hydroxy-17-(pentafluoroethyl)-11-(4-{[(pyridin-4-ylmethyl)amino]methyl}phenyl)estra-4,9-dien-3-one | 588, 0.96 min. |
| 48 | 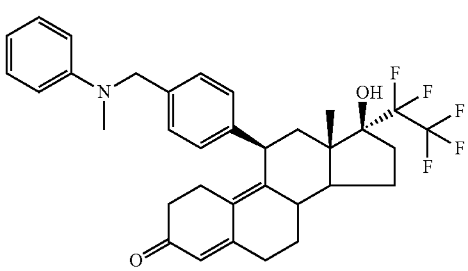 [SMILES: CN(Cc1ccc([C@H]2C[C@@]3(C)C(CC[C@@]3(O)C(F)(F)C(F)(F)F)C3CCC4=CC(=O)CCC4=C32)cc1)c1ccccc1] | (11β,17β)-17-Hydroxy-11-(4-{[methyl(phenyl)amino]methyl}phenyl)-17-(pentafluoroethyl)estra-4,9-dien-3-one | 587, 1.55 min. |

-continued

| Ex. | Structure | Name | HPLC-MS (MH+, RT) |
|---|---|---|---|
| 49 | 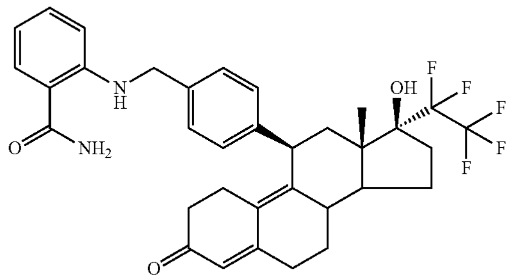 [SMILES: C[C@]12C[C@H](c3ccc(CNc4ccccc4C(N)=O)cc3)C3=C4CCC(=O)C=C4CCC3C1CC[C@@]2(O)C(F)(F)C(F)(F)F] | 2-({4-[(11β,17β)-17-Hydroxy-3-oxo-17-(pentafluoroethyl)estra-4,9-dien-11-yl]benzyl}amino)benzamide | 616, 1.38 min. |
| 50 | 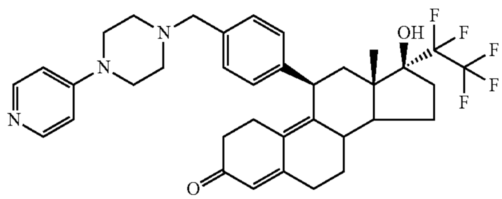 [SMILES: C[C@]12C[C@H](c3ccc(CN4CCN(c5ccncc5)CC4)cc3)C3=C4CCC(=O)C=C4CCC3C1CC[C@@]2(O)C(F)(F)C(F)(F)F] | (11β,17β)-17-Hydroxy-17-(pentafluoroethyl)-11-(4-{[4-(pyridin-4-yl)piperazin-1-yl]methyl}phenyl)estra-4,9-dien-3-one | 643, 0.87 min. |
| 51 | 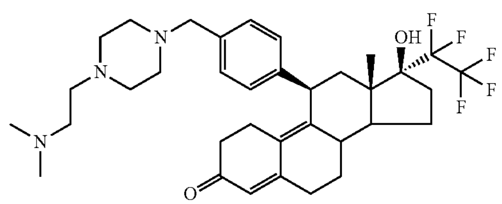 [SMILES: CN(C)CCN1CCN(Cc2ccc([C@H]3C[C@@]4(C)C(CC[C@@]4(O)C(F)(F)C(F)(F)F)C4CCC5=CC(=O)CCC5=C43)cc2)CC1] | (11β,17β)-11-[4-({4-[2-(Dimethylamino)ethyl]piperazin-1-yl}methyl)phenyl]-17-hydroxy-17-(pentafluoroethyl)estra-4,9-dien-3-one | 637, 0.85 min. |
| 52 | 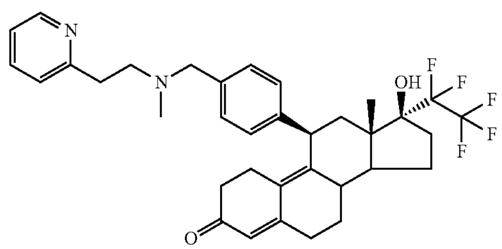 [SMILES: CN(CCc1ccccn1)Cc1ccc([C@H]2C[C@@]3(C)C(CC[C@@]3(O)C(F)(F)C(F)(F)F)C3CCC4=CC(=O)CCC4=C32)cc1] | (11β,17β)-17-Hydroxy-11-[4-({methyl[2-(pyridin-2-yl)ethyl]amino}methyl)phenyl]-17-(pentafluoroethyl)estra-4,9-dien-3-one | 616, 1.04 min. |
| 53 | 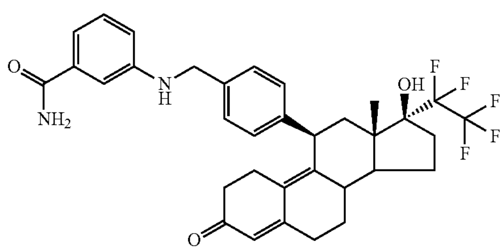 [SMILES: C[C@]12C[C@H](c3ccc(CNc4cccc(C(N)=O)c4)cc3)C3=C4CCC(=O)C=C4CCC3C1CC[C@@]2(O)C(F)(F)C(F)(F)F] | 3-({4-[(11β,17β)-17-Hydroxy-3-oxo-17-(pentafluoroethyl)estra-4,9-dien-11-yl]benzyl}amino)benzamide | 616, 1.29 min. |
| 54 | 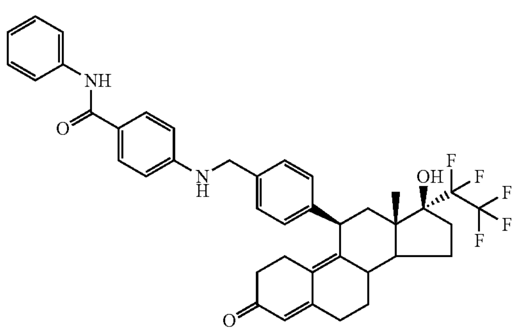 [SMILES: C[C@]12C[C@H](c3ccc(CNc4ccc(C(=O)Nc5ccccc5)cc4)cc3)C3=C4CCC(=O)C=C4CCC3C1CC[C@@]2(O)C(F)(F)C(F)(F)F] | 4-({4-[(11β,17β)-17-Hydroxy-3-oxo-17-(pentafluoroethyl)estra-4,9-dien-11-yl]benzyl}amino)-N-phenylbenzamide | 692, 1.41 min. |

Progesterone Receptor Antagonistic Effect in Stable Transfectants of Human Neuroblastoma Cells (SK-N-MC cells) with the Human Progesterone A or Progesterone B Receptor and a MTV-LUC Reporter Construct SK-N-MC cells (human neuroblastoma cells), which have been stably transfected with plasmids which express the human progesterone receptor B (pRChPR-B-neo) or the human progesterone receptor A (pRChPR-A-neo) and a reporter construct (pMMTV-LUC), were incubated for 24 hours either in the absence (negative control) or in the presence of increasing amounts of the particular test compound (0.01 nmol/l, 0.1 nmol/l, 1 nmol/l, 10 nmol/l, 100 nmol/l and 1 μmol/l) in order to determine the agonistic efficacy. As a positive control of the reporter gene induction, the cells were treated with the synthetic gestagen promegestone (0.01 nmol/l, 0.1 nmol/l, 1 nmol/l, 10 nmol/l, 100 nmol/l and 1 μmol/l). To determine the antagonistic activity, the cells were treated with 0.1 nmol/l of promegestone and additionally with increasing amounts of the particular test compound (0.01 nmol/l, 0.1 nmol/l, 1 nmol/l, 10 nmol/l, 100 nmol/l and 1 μmol/l). The activity of the reporter gene LUC (LUC=luciferase) was determined in the cell lysates and measured as RLU (relative light units). All measurement values are given as percentage efficacy and as $EC_{50}$ or $IC_{50}$ concentrations.

a) Agonistic Activity:

None of the stated test compounds exhibits an agonistic activity.

b) Antagonistic Activity:

All of the stated compounds exhibit a 100% antagonistic effectiveness.

The antagonistic potency of the compounds is summarized in Table 1.

TABLE 1

Antagonistic potency of the compounds

| Ex. | PR-A $IC_{50}$ [nM] | PR-B $IC_{50}$ [nM] |
|---|---|---|
| 1 | 7.5 | 8.2 |
| 2 | 3.5 | 2.8 |
| 3 | 0.11 | 0.15 |
| 4 | 1.4 | 2.1 |
| 5 | 1.2 | 0.99 |
| 6 | 0.33 | 0.3 |
| 7 | 0.1 | 0.1 |
| 8 | 0.1 | 0.3 |
| 9 | 1.3 | 0.98 |
| 10 | 0.88 | 0.12 |
| 11 | 0.095 | 0.095 |
| 12 | 0.17 | 0.1 |
| 13 | 0.092 | 0.1 |
| 14 | 0.1 | 0.094 |
| 15 | 53 | 60 |
| 16 | 2.7 | 2.8 |
| 17 | 0.56 | 0.57 |
| 18 | 0.51 | n.d. |
| 19 | 0.94 | n.d. |
| 20 | 1.64 | n.d. |
| 21 | 6.06 | n.d. |
| 22 | 2.52 | n.d. |
| 23 | 2.07 | n.d. |
| 24 | 51 | n.d. |
| 25 | 3.06 | n.d. |
| 26 | 4.65 | n.d. |
| 27 | 3.52 | n.d. |
| 28 | 5.05 | n.d. |
| 29 | 1.19 | n.d. |
| 30 | 2.35 | n.d. |
| 31 | 4.52 | n.d. |
| 32 | 0.78 | n.d. |
| 33 | 5.57 | n.d. |

TABLE 1-continued

Antagonistic potency of the compounds

| Ex. | PR-A $IC_{50}$ [nM] | PR-B $IC_{50}$ [nM] |
|---|---|---|
| 34 | 5.55 | n.d. |
| 35 | 0.68 | n.d. |
| 36 | 33.7 | n.d. |
| 37 | 2.33 | n.d. |
| 38 | 0.66 | n.d. |
| 39 | 1.77 | n.d. |
| 40 | 0.49 | n.d. |
| 41 | 11.2 | n.d. |
| 42 | 0.52 | n.d. |
| 43 | 2.88 | n.d. |
| 44 | 3.06 | n.d. |
| 45 | 1.65 | n.d. |
| 46 | 37.4 | n.d. |
| 47 | 2.71 | n.d. |
| 48 | 1.28 | n.d. |
| 49 | 1.29 | n.d. |
| 50 | 1.20 | n.d. |
| 51 | 64.7 | n.d. |
| 52 | 6.50 | n.d. |
| 53 | 0.84 | n.d. |
| 54 | 1.28 | n.d. | n.d.: not determined

Abortive Test on Female Rats

The antagonistic effect of the compounds according to the invention was tested on pregnant rats (6 rats per group) on day (d) 5 to 7 post coitum (p.c.) under conventional keeping and feeding conditions.

After successful pairing, the pregnant animals (presence of sperm in the vaginal smear on day 1 of the pregnancy=d1 p.c.) were randomized and divided into the treatment group and the control group. The animals were then given, subcutaneously or orally, in each case 0.15; 0.5; 1.5 or 5 mg/kg of the test compound or 1.0 nil/kg of vehicle (benzyl benzoate/ricinus oil: 1+4 [v/v]) daily from day 5 to day 7 (d5-d7 p.c.).

The autopsy was carried out on day 9 (d9 p.c.). As the parameter of the progesterone receptor antagonistic effect, the uterus was investigated with regard to the presence of nidation sites. Here, the complete lack of nidation sites, but also the presence of pathological, haemmorhagic or otherwise abnormal nidation sites, on day 9 (d9 p.c.) was evaluated as an abortion. The results of the tests are shown in Table 3. The test compound exhibits a full effect at all dosages.

TABLE 2

Results on rat (termination of early pregnancy)

| Test compound after | Daily dose [mg/kg] p.o. | Abortion rate [%] |
|---|---|---|
| Vehicle | | 0 |
| Example 11 (11β,17β)-11-{4-[(4-Acetyl-piperazin-1-yl)methyl]-phenyl}-17-hydroxy-17-(pentafluoroethyl)estra-4,9-dien-3-one | 0.5 | 100 |
| | 1.5 | 100 |
| | 5.0 | 100 |
| Example 12 (11β,17β)-17-Hydroxy-11-(4-{[4-(methylsulphonyl)piperazin-1-yl]methyl}phenyl)-17- | 0.5 | 100 |
| | 1.5 | 100 |
| | 5.0 | 100 |

TABLE 2-continued

Results on rat (termination of early pregnancy)

| Test compound after | Daily dose [mg/kg] p.o. | Abortion rate [%] |
|---|---|---|
| (pentafluoroethyl)estra-4,9-dien-3-one | | | p.o.: per oral

The invention claimed is:

1. A compound that is a 17-hydroxy-17-pentafluoroethyl-estra-4,9(10)-dien-11-aryl derivative of the general formula I

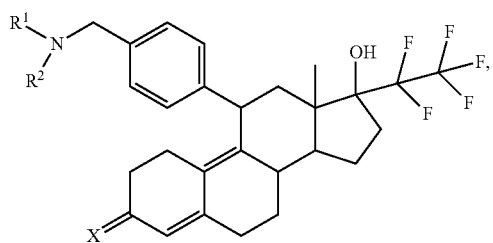

in which
R$^1$ and R$^2$
are identical or different and are
hydrogen,
an optionally dimethylamine-substituted C$_1$-C$_{10}$-alkyl radical,
a 6-10-membered aryl radical optionally mono-, di- or polysubstituted with halogen, —OH, —O-alkyl, —C(O)OH, —C(O)Oalkyl, —C(O)NH$_2$, —C(O)NHalkyl, —C(O)Ndialkyl, —C(O)NHaryl, —C(O)NHheteroaryl, —NH$_2$, —NH(C$_1$-C$_{10}$-alkyl), —N(C$_1$-C$_{10}$-alkyl)$_2$, —NHC(O)alkyl, —NO$_2$, —N$_3$, —CN, —C$_1$-C$_{10}$-alkyl, —C$_1$-C$_{10}$-perfluoro alkyl, —C$_1$-C$_{10}$-acyl, —C$_1$-C$_{10}$-acyloxy, —SO$_2$NH$_2$, —SO$_2$NHalkyl
or —SO$_2$Ndialkyl,
a 5-10-membered heteroaryl radical optionally mono-, di- or polysubstituted with the aforementioned substituents of the 6-10-membered aryl radical,
a C$_1$-C$_6$-arylalkyl radical optionally mono-, di- or polysubstituted on the aryl ring with the aforementioned substituents of the 6-10-membered aryl radical
or
a C$_1$-C$_6$-heteroarylalkyl radical optionally mono-, di- or polysubstituted on the heteroaryl ring with the aforementioned substituents of the 6-10-membered aryl radical,
or else
R$^1$ and R$^2$
are together a constituent of a 3-10-membered ring which is optionally substituted on the carbon by alkyl, carboxyl, alkoxycarbonyl, alkylcarbonyl, aminocarbonyl, arylalkyl, heteroarylalkyl, aminoalkyl and/or on the nitrogen by alkyl, alkanoyl, carboxyl, alkoxycarbonyl, phenyl, phenylalkyl, pyridinyl, pyrimidinyl, pyrazinyl, sulphonyl, benzoyl, alkylsulphonyl, arylsulphonyl, aminocarbonyl, aminocarbonylalkyl, arylalkyl, heteroarylalkyl, heterocyclylalkyl and aminoalkyl, and which optionally contains nitrogen, oxygen or sulphur atoms which is optionally oxidized with the sulphoxide or sulphone, where an aromatic is optionally fused onto the 3-10-membered ring,
X is an oxygen atom or NOR$^3$ or NNHSO$_2$R$^3$,
R$^3$ is hydrogen, C$_1$-C$_{10}$-alkyl, or aryl, or a salt thereof.

2. The compound according to claim 1 of the general formula II

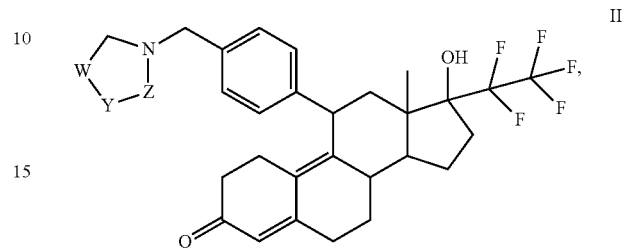

in which
Z is —CH$_2$—, —CH$_2$—CH$_2$— or —CH$_2$—CH$_2$—CH$_2$—,
W is —CH$_2$—,
Y is —CHR$^4$—, —NR$^5$—, —O— or —SO$_2$— or
W and Y
together are a constituent of a fused aromatic ring,
R$^4$ and R$^5$
are hydrogen, —C$_1$-C$_4$-alkyl, —(CH$_2$)$_m$-phenyl, —(CH$_2$)$_m$-pyridinyl, —(CH$_2$)$_m$-pyrazinyl, —(CH$_2$)$_m$—NR$^7$R$^8$, —(CH$_2$)$_m$—C(O)—R$^6$ where m=0, 1, 2 or 3 or —SO$_2$—C$_1$-C$_4$-alkyl,
R$^6$ is —OH, —C$_1$-C$_4$-alkyl, —O—C$_1$-C$_4$-alkyl, -phenyl or —NR$^7$R$^8$ and
R$^7$, R$^8$ independently of one another are hydrogen or —C$_1$-C$_4$-alkyl or together are a constituent of a 5- to 7-membered ring or a salt thereof.

3. The compound according to claim 2
in which
Z is —CH$_2$—CH$_2$— or —CH$_2$—CH$_2$—CH$_2$—,
W is —CH$_2$—,
Y is —CHR$^4$—, —NR$^5$—,
R$^4$ and R$^5$
are —C(O)—R$^6$ or —SO$_2$—C$_1$-C$_4$-alkyl and
R$^6$ is —OH, —C$_1$-C$_4$-alkyl, —O—C$_1$-C$_4$-alkyl
or a salt thereof.

4. The compound according to claim 1
in which
R$^1$ and R$^2$
are identical or different and, independently of one another, are C$_1$-C$_4$-alkyl radical, di—C$_1$-C$_4$-alkylamino—C$_1$-C$_4$-alkyl radical, an optionally halogen-, C$_1$-C$_4$-alkoxy-, —SO$_2$NH$_2$—, —C(O)NH$_2$—, —C(O)O—C$_1$-C$_4$-alkyl-, —NH—C(O)—C$_1$-C$_4$-alkyl- or —C(O)—NH-phenyl-substituted phenyl or C$_1$-C$_4$-alkylphenyl radical or an optionally halogen-, C$_1$-C$_4$-alkoxy-, —SO$_2$NH$_2$—, —C(O)NH$_2$—, —C(O)O—C$_1$-C$_4$-alkyl-, —NH—C(O)—C$_1$-C$_4$-alkyl- or —C(O)—NH-phenyl-substituted pyridyl or C$_1$-C$_4$-alkylpyridyl radical,
or a salt thereof.

5. The compound according to claim 4 in which
R$^1$ is hydrogen or C$_1$-C$_4$-alkyl and
R$^2$ is hydrogen;
C$_1$-C$_4$-alkyl,
dimethylamino—C$_1$-C$_4$-alkyl, an optionally halogen-, alkoxy-, —SO$_2$NH$_2$—, —C(O)NH$_2$—, —C(O)O—C$_1$-C$_4$-alkyl-, —NH—C(O)—C$_1$-C$_4$-alkyl- or —C(O)—NH-phenyl-substituted phenyl radical,
—C$_1$-C$_4$-alkylphenyl,
pyridyl or
—C$_1$-C$_4$-alkylpyridyl
or a salt thereof.

6. The compound according to claim 4 in which R$^1$ is hydrogen, methyl or ethyl, or a salt thereof.

7. The compound according to claim 4 in which R$^2$ is —CH$_3$, —CH$_2$CH$_3$, —CH$_2$—CH$_2$—N(CH$_3$)$_2$, a —(CH$_2$)$_n$-phenyl radical optionally substituted on the phenyl ring with Cl—, —OCH$_3$, —SO$_2$NH$_2$, —C(O)NH$_2$, —CO$_2$CH$_3$, —NH—C(O)CH$_3$ or —C(O)—NH-phenyl, or a —(CH$_2$)$_n$-pyridyl where n=0, 1, 2, or a salt thereof.

8. The compound according to claim 4, in which
R$^1$ is hydrogen, methyl or ethyl and
R$^2$ is —CH$_3$, —CH$_2$CH$_3$, —CH$_2$—CH$_2$—N(CH$_3$)$_2$, a —(CH$_2$)$_n$-phenyl radical optionally substituted on the phenyl ring with Cl—, —OCH$_3$, —SO$_2$NH$_2$, —C(O)NH$_2$, —C(O)OCH$_3$, —NH—C(O)CH$_3$ or —C(O)—NH-phenyl, or a —(CH$_2$)$_n$-pyridyl where n=0, 1, 2 or a salt thereof.

9. The compound according to claim 1, wherein the compound is selected from the group consisting of:
(11β,17β)-11-{4-[(dimethylamino)methyl]phenyl}-17-hydroxy-17-(pentafluoroethyl)estra-4,9-dien-3-one;
(11β,17β)-17-hydroxy-11-{4-[(4-methylpiperazin-1-yl)methyl]phenyl}-17-(pentafluoroethyl)estra-4,9-dien-3-one;
tert-butyl 4-{4-[(11β,17β)-17-hydroxy-3-oxo-17-(pentafluoroethyl)estra-4,9-dien-11-yl]benzyl}piperazine-1-carboxylate;
(11β,17β)-17-hydroxy-17-(pentafluoroethyl)-11-[4-(piperidin-1-ylmethyl)phenyl]estra-4,9-dien-3-one;
methyl 1-{4-[(11β,17β)-17-hydroxy-3-oxo-17-(pentafluoroethyl)estra-4,9-dien-11-yl]benzyl}piperidine-4-carboxylate;
tert-butyl 4-{4-[(11β,17β)-17-hydroxy-3-oxo-17-(pentafluoroethyl)estra-4,9-dien-11-yl]benzyl}-1,4-diazepane-1-carboxylate;
(11β,17β)-17-hydroxy-11-[4-(morpholin-4-ylmethyl)phenyl]-17-(pentafluoroethyl)estra-4,9-dien-3-one;
(11β,17β)-11-{4-[(1,1-dioxidothiomorpholin-4-yl)methyl]phenyl}-17-hydroxy-17-(pentafluoroethyl)estra-4,9-dien-3-one;
(11β,17β)-17-hydroxy-17-(pentafluoroethyl)-11-(4-{[(2-phenylethyl)amino]methyl}phenyl)estra-4,9-dien-3-one;
(11β,17β)-17-hydroxy-17-(pentafluoroethyl)-11-[4-(piperazin-1-ylmethyl)phenyl]estra-4,9-dien-3-one;
(11β,17β)-11-{4-[(4-acetylpiperazin-1-yl)methyl]phenyl}-17-hydroxy-17-(pentafluoroethyl)estra-4,9-dien-3-one;
(11β,17β)-17-hydroxy-11-(4-{[4-(methylsulphonyl)piperazin-1-yl]methyl}phenyl)-17-(pentafluoroethyl)estra-4,9-dien-3-one;
(11β,17β)-11-{4-[(4-benzoylpiperazin-1-yl)methyl]phenyl}-17-hydroxy-17-(pentafluoroethyl)estra-4,9-dien-3-one;
(11β,17β)-11-(4-{[4-(2,2-dimethylpropanoyl)piperazin-1-yl]methyl}phenyl)-17-hydroxy-17-(pentafluoroethyl)estra-4,9-dien-3-one;
1-{4-[(11β,17β)-17-hydroxy-3-oxo-17-(pentafluoroethyl)estra-4,9-dien-11-yl]benzyl}piperidine-4-carboxylic acid;
(11β,17β)-11-[4-(1,4-diazepan-1-ylmethyl)phenyl]-17-hydroxy-17-(pentafluoroethyl)estra-4,9-dien-3-one;
(11β,17β)-11-{4-[(4-acetyl-1,4-diazepan-1-yl)methyl]phenyl}-17-hydroxy-17-(pentafluoroethyl)estra-4,9-dien-3-one;
4-({4-[(11β,17β)-17-hydroxy-3-oxo-17-(pentafluoroethyl)estra-4,9-dien-11-yl]benzyl}amino)benzenesulphonamide;
(11β,17β)-17-hydroxy-17-(pentafluoroethyl)-11-{4-[(pyridin-3-ylamino)methyl]phenyl}estra-4,9-dien-3-one;
(11β,17β)-11-[4-(anilinomethyl)phenyl]-17-hydroxy-17-(pentafluoroethyl)estra-4,9-dien-3-one;
(11β,17β)-17-hydroxy-11-(4-{[(2-methoxyphenyl)amino]methyl}phenyl)-17-(pentafluoroethyl)estra-4,9-dien-3-one;
(11β,17β)-17-hydroxy-11-(4-{[(3-methoxyphenyl)amino]methyl}phenyl)-17-(pentafluoroethyl)estra-4,9-dien-3-one;
(11β,17β)-11-(4-{[(4-chlorophenyl)amino]methyl}phenyl)-17-hydroxy-17-(pentafluoroethyl)estra-4,9-dien-3-one;
(11β,17β)-11-{4-[(diethylamino)methyl]phenyl}-17-hydroxy-17-(pentafluoroethyl)estra-4,9-dien-3-one;
(11β,17β)-17-hydroxy-17-(pentafluoroethyl)-11-{4-[(4-phenylpiperazin-1-yl)methyl]phenyl}estra-4,9-dien-3-one;
(11β,17β)-17-hydroxy-11-(4-{[methyl(pyridin-4-ylmethyl)amino]methyl}phenyl)-17-(pentafluoroethyl)estra-4,9-dien-3-one;
(11β,17β)-11-[4-({[2-(dimethylamino)ethyl](methyl)amino}methyl)phenyl]-17-hydroxy-17-(pentafluoroethyl)estra-4,9-dien-3-one;
methyl 2-({4-[(11β,17β)-17-hydroxy-3-oxo-17-(pentafluoroethyl)estra-4,9-dien-11-yl]benzyl}amino)benzoate;
methyl 4-({4-[(11β,17β)-17-hydroxy-3-oxo-17-(pentafluoroethyl)estra-4,9-dien-11-yl]benzyl}amino)benzoate;
(11β,17β)-11-[4-(3,4-dihydroisoquinolin-2(1H)-ylmethyl)phenyl]-17-hydroxy-17-(pentafluoroethyl)estra-4,9-dien-3-one;
(11β,17β)-11-{4-[(4-benzylpiperazin-1-yl)methyl]phenyl}-17-hydroxy-17-(pentafluoroethyl)estra-4,9-dien-3-one;
4-({4-[(11β,17β)-17-hydroxy-3-oxo-17-(pentafluoroethyl)estra-4,9-dien-11-yl]benzyl}amino)benzamide;
(11β,17β)-17-hydroxy-11-(4-{[methyl(2-phenylethyl)amino]methyl}phenyl)-17-(pentafluoroethyl)estra-4,9-dien-3-one;
(11β,17β)-17-hydroxy-17-(pentafluoroethyl)-11-(4-{[4-(2-phenylethyl)piperazin-1-yl]methyl}phenyl)estra-4,9-dien-3-one;
(11β,17β)-17-hydroxy-17-(pentafluoroethyl)-11-(4-{[4-(pyrazin-2-yl)piperazin-1-yl]methyl}phenyl)estra-4,9-dien-3-one;
(11β,17β)-17-hydroxy-17-(pentafluoroethyl)-11-[4-({4-[2-(pyrrolidin-1-yl)ethyl]piperazin-1-yl}methyl)phenyl]estra-4,9-dien-3-one;
(11β,17β)-17-hydroxy-17-(pentafluoroethyl)-11-(4-{[4-(pyridin-4-ylmethyl)piperazin-1-yl]methyl}phenyl)estra-4,9-dien-3-one;
N-[4-({4-[(11β,17β)-17-hydroxy-3-oxo-17-(pentafluoroethyl)estra-4,9-dien-11-yl]benzyl}amino)phenyl]acetamide;
methyl 3-({4-[(11β,17β)-17-hydroxy-3-oxo-17-(pentafluoroethyl)estra-4,9-dien-11-yl]benzyl}amino)benzoate;

3-({4-[(11β,17β)-17-hydroxy-3-oxo-17-(pentafluoroethyl)estra-4,9-dien-11-yl]benzyl}amino)benzenesulphonamide;

(11β,17β)-17-hydroxy-17-(pentafluoroethyl)-11-{4-[(4-phenylpiperidin-1-yl)methyl]phenyl}estra-4,9-dien-3-one;

4-{4-[(11β,17β)-17-hydroxy-3-oxo-17-(pentafluoroethyl)estra-4,9-dien-11-yl]benzyl}-N,N-dimethylpiperazine-1-carboxamide;

(11β,17β)-17-hydroxy-17-(pentafluoroethyl)-11-(4-{[4-(pyridin-2-ylmethyl)piperazin-1-yl]methyl}phenyl)estra-4,9-dien-3-one;

(11β,17β)-17-hydroxy-17-(pentafluoroethyl)-11-(4-{[4-(pyridin-3-ylmethyl)piperazin-1-yl]methyl}phenyl)estra-4,9-dien-3-one;

2-(4-{4-[(11β,17β)-17-hydroxy-3-oxo-17-(pentafluoroethyl)estra-4,9-dien-11-yl]benzyl}piperazin-1-yl)-N-methylacetamide;

(11β,17β)-17-hydroxy-17-(pentafluoroethyl)-11-[4-(pyrrolidin-1-ylmethyl)phenyl]estra-4,9-dien-3-one;

(11β,17β)-17-hydroxy-17-(pentafluoroethyl)-11-[4-{(pyridin-4-ylmethyl)amino]methyl}phenyl)estra-4,9-dien-3-one;

(11β,17β)-17-hydroxy-11-(4-{[methyl(phenyl)amino]methyl}phenyl)-17-(pentafluoroethyl)estra-4,9-dien-3-one;

2-({4-[(11β,17β)-17-hydroxy-3-oxo-17-(pentafluoroethyl)estra-4,9-dien-11-yl]benzyl}amino)benzamide;

(11β,17β)-17-hydroxy-17-(pentafluoroethyl)-11-(4-{[4-(pyridin-4-yl)piperazin-1-yl]methyl}phenyl)estra-4,9-dien-3-one;

(11β,17β)-11-[4-({4-[2-(dimethylamino)ethyl]piperazin-1-yl}methyl)phenyl]-17-hydroxy-17-(pentafluoroethyl)estra-4,9-dien-3-one;

(11β,17β)-17-hydroxy-11-[4-({methyl[2-(pyridin-2-yl)ethyl]amino}methyl)phenyl]-17-(pentafluoroethyl)estra-4,9-dien-3-one;

3-({4-[(11β,17β)-17-hydroxy-3-oxo-17-(pentafluoroethyl)estra-4,9-dien-11-yl]benzyl}amino)benzamide; and 4-({4-[(11β,17β)-17-hydroxy-3-oxo-17-(pentafluoroethyl)estra-4,9-dien-11-yl]benzyl}amino)-N-phenylbenzamide, or a salt thereof.

10. A method for producing a medicament for the treatment of uterus fibroids, endometriosis, heavy menstrual bleeding, mengiomas, breast cancers or emergency contraception, comprising combining the compound of claim 1 with an inert, nontoxic, pharmaceutically suitable auxiliary.

11. A medicament comprising the compound of claim 1 and a further active ingredient.

12. The medicament according to claim 11 further comprising an inert, nontoxic, pharmaceutically suitable auxiliary.

13. A method for the treatment of uterus fibroids, endometriosis, heavy menstrual bleeding, meningiomas, breast cancers or, or for providing emergency contraception, the method comprising administering a therapeutically effective amount of the compound of claim 1 to a human or animal in need thereof.

14. A method for the treatment of endometriosis or uterus fibroids comprising administering a therapeutically effective amount of the compound of claim 1 to a human or animal in need thereof.

15. A method of contraception comprising administering a therapeutically effective amount of the compound of claim 1 to a human or animal in need thereof.

* * * * *